(12) United States Patent
Thimmaiah et al.

(10) Patent No.: US 10,544,167 B2
(45) Date of Patent: Jan. 28, 2020

(54) COMPOUNDS AS STIMULI-RESPONSIVE PROBES, METHODS AND APPLICATIONS THEREOF

(71) Applicant: JAWAHARLAL NEHRU CENTRE FOR ADVANCED SCIENTIFIC RESEARCH, Bangalore, Karnataka (IN)

(72) Inventors: Govindaraju Thimmaiah, Bengaluru (IN); Nagarjun Narayanaswamy, Bengaluru (IN)

(73) Assignee: Jawaharlal Nehru Centre for Advanced Scientific Research, Bangalore, Karnataka (IN)

( * ) Notice: Subject to any disclaimer, the term of this patent is extended or adjusted under 35 U.S.C. 154(b) by 0 days.

(21) Appl. No.: 15/755,283

(22) PCT Filed: Aug. 26, 2016

(86) PCT No.: PCT/IB2016/055114
§ 371 (c)(1),
(2) Date: Feb. 26, 2018

(87) PCT Pub. No.: WO2017/033163
PCT Pub. Date: Mar. 2, 2017

(65) Prior Publication Data
US 2018/0251478 A1 Sep. 6, 2018

(30) Foreign Application Priority Data
Aug. 26, 2015 (IN) .............................. 4494/CHE/2015

(51) Int. Cl.
*C07F 5/02* (2006.01)
*G01N 33/52* (2006.01)
*A61K 31/69* (2006.01)
*A61K 49/00* (2006.01)

(52) U.S. Cl.
CPC .............. *C07F 5/025* (2013.01); *A61K 31/69* (2013.01); *G01N 33/52* (2013.01); *A61K 49/0032* (2013.01); *A61K 2123/00* (2013.01)

(58) Field of Classification Search
CPC .................................. C07F 5/02; G01N 33/52
See application file for complete search history.

(56) References Cited

PUBLICATIONS

Han Junyan et al., A Non-toxic Fluorogenic Dye for Mitochondria Labeling, Biochimica et Biphysica Acta, 1830 (11), 5130-5135. (Year: 2013).*
Han, Junyan et al.: "A Non-Toxic Fluorogenic Dye for Mitochondria Labeling," Biochimica Et Biophysica Acta, General Subjects, 1830(11), 5130-5135 Coden: BBGSB3; ISSN: 0304-4165, 2013, XP002762884, 6 pages.
International Search Report and Written Opinion issued for PCT/IB2016/055114, dated Oct. 24, 2016, 12 pages.

* cited by examiner

*Primary Examiner* — Michael G. Hartley
*Assistant Examiner* — Jagadishwar R Samala
(74) *Attorney, Agent, or Firm* — Foley & Lardner LLP

(57) ABSTRACT

The present disclosure relates to the field of synthetic pharmaceutical chemistry and biology. The disclosure provides a compound of Formula I and a process of preparation thereof. The disclosure further relates to methods and use of Formula I compounds as stimuli-responsive probes. Said Formula I compounds are employed for detecting and quantifying reactive oxygen species (ROS), and have related applications including but not limited fluorescence spectroscopy, diagnostics, treatment, imaging and biomedical applications.

14 Claims, 16 Drawing Sheets

COMPOUNDS AS STIMULI-RESPONSIVE PROBES, METHODS AND APPLICATIONS THEREOF

CROSS-REFERENCE TO RELATED APPLICATIONS

This application is a U.S. National Phase Application under 35 U.S.C. § 371 of International Application No. PCT/IB2016/055114, filed on Aug. 26, 2016, which claims the benefit of priority to Indian Application No. 4494/CHE/2015, filed on Aug. 26, 2015, the entire contents of which are incorporated herein by reference in their entireties.

The following specification particularly describes the invention and the manner in which it is to be performed.

TECHNICAL FIELD

The present disclosure relates to the field of synthetic pharmaceutical chemistry and biology. In particular, a compound of Formula I and a process of preparation thereof are disclosed. The disclosure further relates to methods and use of Formula I compounds as stimuli-responsive probes. Said Formula I compounds are employed for detecting ROS, and have related applications including but not limited to fluorescence spectroscopy, diagnostics, imaging and biomedical applications.

BACKGROUND OF THE DISCLOSURE

The regulation of redox homeostasis is essential for maintaining normal cellular functions such as signaling, growth, survival and death. Anomalous behavior of redox homeostasis adversely affects the normal physiological functions and is in turn responsible for numerous pathological conditions. Normally, cells in the diseased state exhibit high levels of aerobic glycolysis (Warburg effect), which results in oxidative stress. For example, the oxidative stress in cancer cells result in the accumulation of high levels of reactive oxygen species (ROS).

ROS constitute an important class of chemically reactive species that are essential for normal cellular functions including cell proliferation and differentiation. The optimum levels of ROS are controlled by various cellular redox homeostasis mechanisms, and an abrupt increase in their concentration levels is directly linked to oxidative stress-related disorders. Abnormally high levels of ROS are generated in response to adverse environmental and physiological stresses, exposure to ultraviolet (UV) light, and ionizing and heat radiations. It is crucial to monitor the levels of intracellular ROS for maintaining effective cellular homeostasis. Notably, different levels of ROS are responsible for different biological responses. Cell maintains different levels of ROS by activating the ROS-scavenging systems such as superoxide dismutases, glutathione peroxidase, redox enzymes (peroxiredoxins, glutaredoxin and thioredoxin) and catalase.

Mis-regulation in any of these ROS-scavenging processes leads to generation of excessive amounts of ROS. Accumulation of high levels of ROS causes oxidative damage of cellular components such as proteins, lipids and nucleic acids, which is responsible for ageing and many pathological conditions including cancer and cardiovascular, inflammatory and neurodegenerative diseases. It is known that cellular aging, also called cellular senescence, is a permanent cell cycle arrest state that results in increased production of ROS species. This increased ROS production is critical in maintaining the viability of the senescent cell. Therefore, it is necessary to develop molecular tools that are highly sensitive and can be activated by high levels of ROS to distinguish aged or diseased and normal cells.

ROS mainly comprises free radicals such as hydroxyl radical (OH.) and superoxide ($O_2.^-$) and reactive molecular species such as $H_2O_2$. $H_2O_2$ is one of the most prominent and essential ROS in biological systems and its significantly higher levels are generated in aged and cancer cells than in normal cells. In fact, $H_2O_2$ is a small molecular metabolite and plays a vital role in the regulation of various physiological processes in living organisms. Most importantly, $H_2O_2$ serves as a messenger in normal cellular signal transduction and is also a known marker for oxidative damage in many disease-associated cells. In cells, $H_2O_2$ is generated through the receptor-mediated NADPH oxidase (Nox) activation, which affects the functioning of signaling proteins that control cell signaling, proliferation, senescence and death.

The biological significance of $H_2O_2$ in human physiology and pathology has generated great interest in understanding the mechanistic details of $H_2O_2$ generation, partition and its role in cellular function and signaling pathways. In comparison to other ROS, relatively higher stability and diffusion rates of $H_2O_2$ through the plasma membrane makes it an attractive candidate to study its signaling pathways in living cells. However, the role of $H_2O_2$ as an essential messenger, for cellular signal transduction and its chemical reactivity and chemical instability limits its spatiotemporal tracking in real-time, especially in living cells. Molecular imaging of $H_2O_2$ using fluorescence probes is a highly attractive tool for studying its generation, accumulation, and trafficking and its role in biological processes in a spatiotemporal manner in living cells.

In recent years, stimuli-responsive fluorescence probes are gaining momentum due to their flexibility in introducing diversity through chemical modification and liberation of biologically active probes at the site of target cellular organelles, in response to biological analytes of interest.

Moreover, targeting specific subcellular organelles (mitochondria) and biomolecules such as DNA and proteins using stimuli-responsive fluorescence probes is an emerging powerful imaging technique that presents enormous potential in biomedical applications related to diagnostics and therapeutics. Therefore, there is a need in the art to develop such stimuli responsive fluorescence probes in order to carry out imaging, biomedical research, diagnosis, treatment etc.

Accordingly, the present disclosure provides for DNA-binding fluorescence probes with a stimuli-responsive appendage, wherein in response to a specific stimulus (chemical or enzyme), the appendage functionality is cleaved to release an NIR-fluorescence ready probe, which upon binding the minor groove of DNA fluoresces strongly, thus, aiding the imaging and quantification of the stimulus.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with the detailed description below, are incorporated in and form part of the specification, and serve to further illustrate the embodiments and explain various principles and advantages, in accordance with the present disclosure where:

FIG. 1(a) depicts the schematic representation of conversion of QCy-BA to p-quinone-methide and QCy-DT, a DNA minor groove binder, in the presence of H$_2$O$_2$.

FIG. 1(b) depicts the time-dependent $^1$H NMR spectral monitoring of slicing of phenyl boronic acid of QCy-BA in the presence of H$_2$O$_2$. Red circles highlight the appearance of new signals for the newly-formed quinone system and QCy-DT. H$_a$ and H$_b$ represent the O—CH$_2$ (C—H$_a$) bearing phenyl boronic acid group and newly formed exocyclic (C—H$_b$) protons of p-quinone-methide, respectively.

FIG. 1(c) depicts the change in solution color upon addition of H$_2$O$_2$ to QCy-BA, as visualized after 2 hours.

FIG. 1(d) Fluorescence response of QCy-BA (5 μM) to various reactive oxygen species (ROS) at individual concentration of 100 μM.

Figure 2:
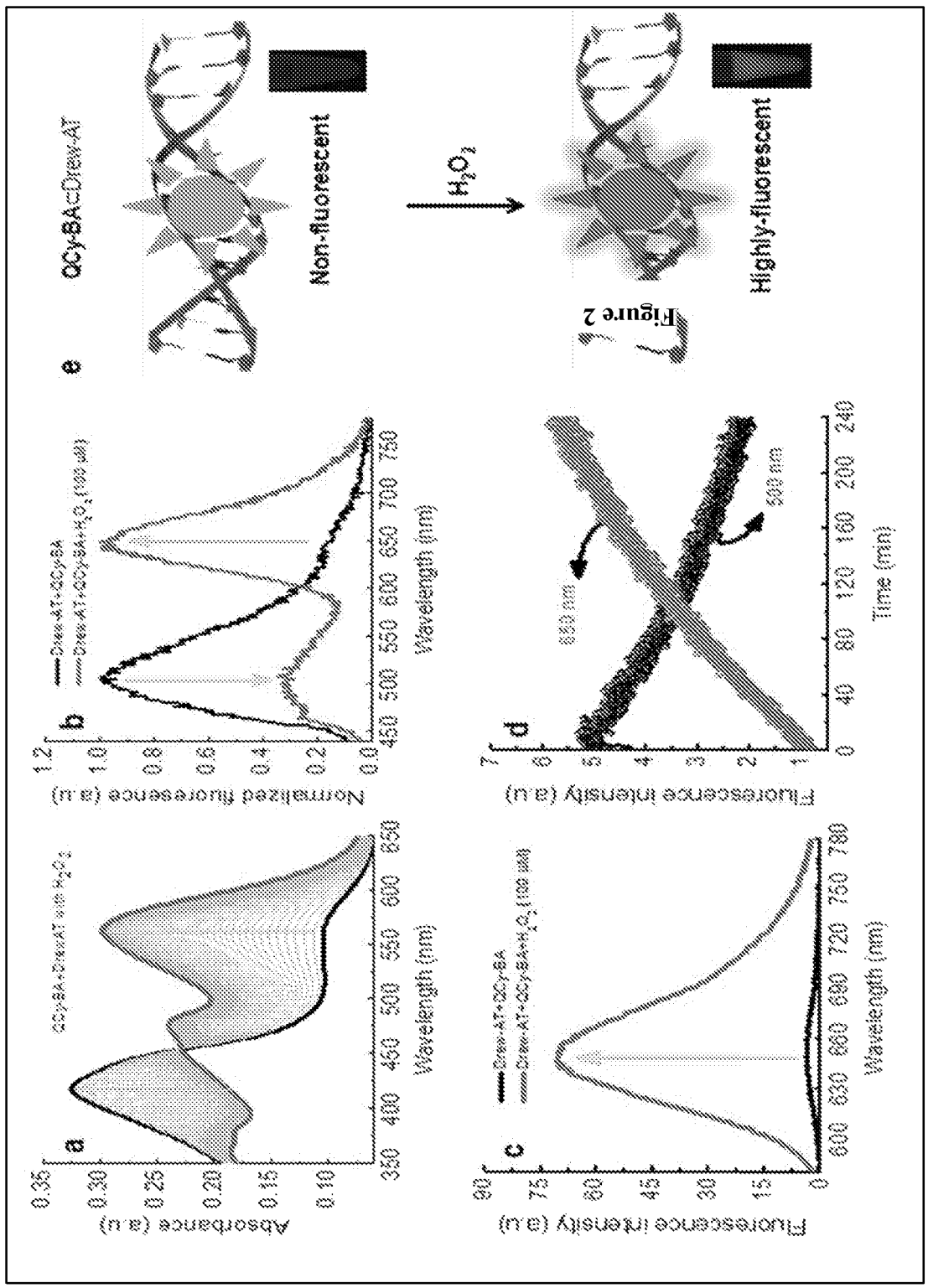

FIG. 2 depicts absorbance and fluorescence response of combination probe QCy-BA ⊂ Drew-AT.

FIG. 2(a) depicts the absorption spectra of combination probe QCy-BA ⊂ Drew-AT (2 μM) in the presence of H$_2$O$_2$ (100 μM) in PBS-buffer solution as a function of time.

FIG. 2(b) depicts the normalized fluorescence spectra of QCy-BA (2 μM) in the presence of Drew-AT (2 μM) upon excitation at 400 nm.

FIG. 2(c) Fluorescence spectra of QCy-BA (2 μM) in the presence of Drew-AT (2 μM) upon excitation at 564 nm. All the spectra are acquired in the presence of H$_2$O$_2$ (100 μM).

FIG. 2(d) depicts the time-dependent fluorescence spectra of QCy-BA (2 μM) in the presence of Drew-AT (2 μM) after the addition of H$_2$O$_2$ (100 μM) upon excitation at 400 nm.

FIG. 2(e) depicts the schematic view of conversion of QCy-BA to p-quinone-methide and a DNA minor groove binder (QCy-DT) with turn-on NIR-fluorescence in the presence of H$_2$O$_2$.

Figure 3:
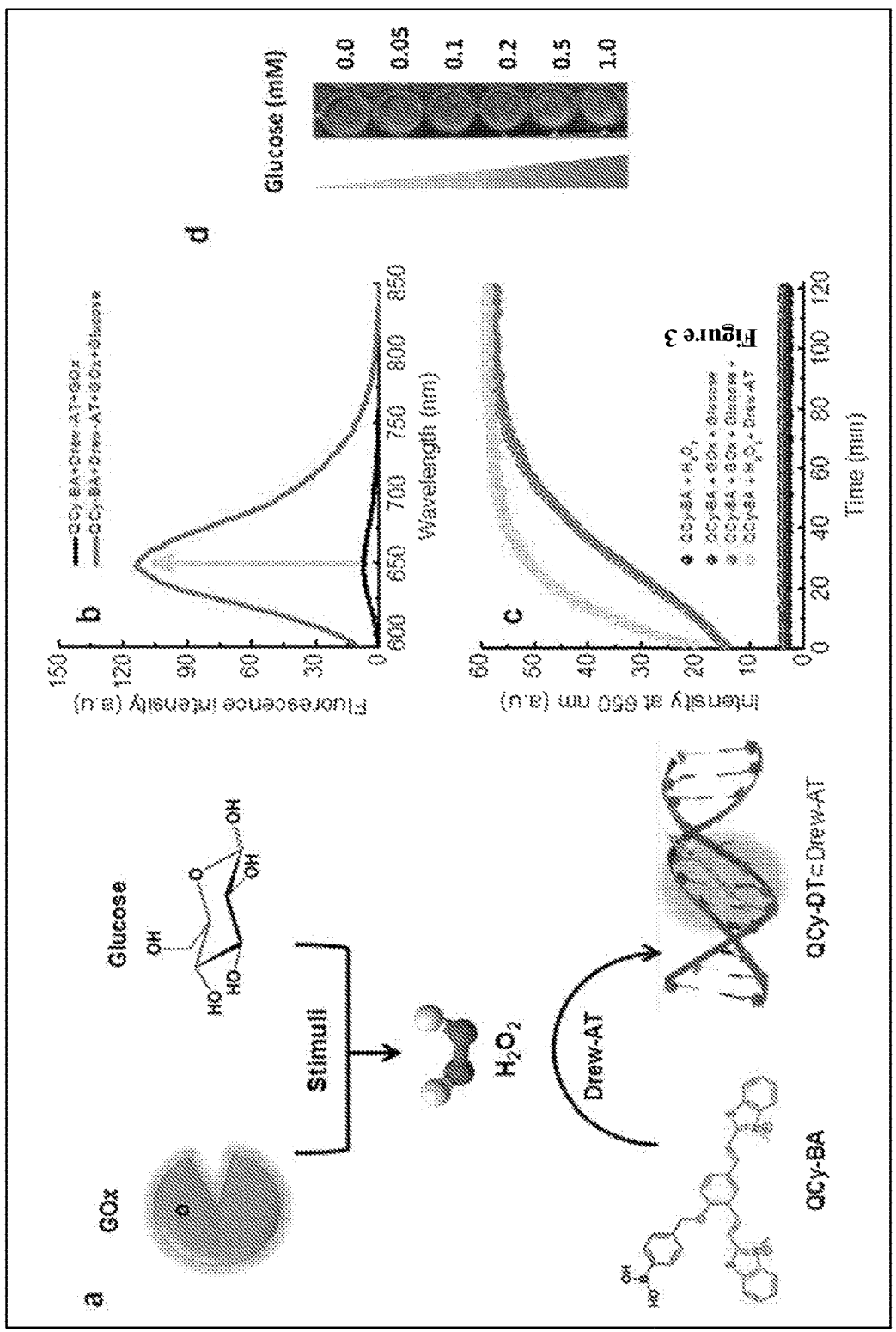

FIG. 3 depicts the glucose oxidase (GOx) assay.

FIG. 3(a) depicts the schematic diagram showing the GOx-assay where Gox oxidizes glucose to gluconic acid, generating H$_2$O$_2$, followed by fluorescence reporting by the combination probe QCy-BA ⊂ Drew-AT.

FIG. 3(b) depicts the fluorescence spectra of combination probe QCy-BA ⊂ Drew-AT in the presence of Gox (4 U/mL) and upon addition of glucose (1 mM).

FIG. 3(c) depicts the time-dependent fluorescence of combination probe QCy-BA ⊂ Drew-AT in the presence and absence of Gox (4 U/mL) upon addition of glucose (1 mM).

FIG. 3(d) depicts the photographs of QCy-BA ⊂ Drew-AT complex under UV-light in the presence of Gox (4 U/mL) with increasing glucose concentration 0.0 to 1.0 mM.

Figure 4:
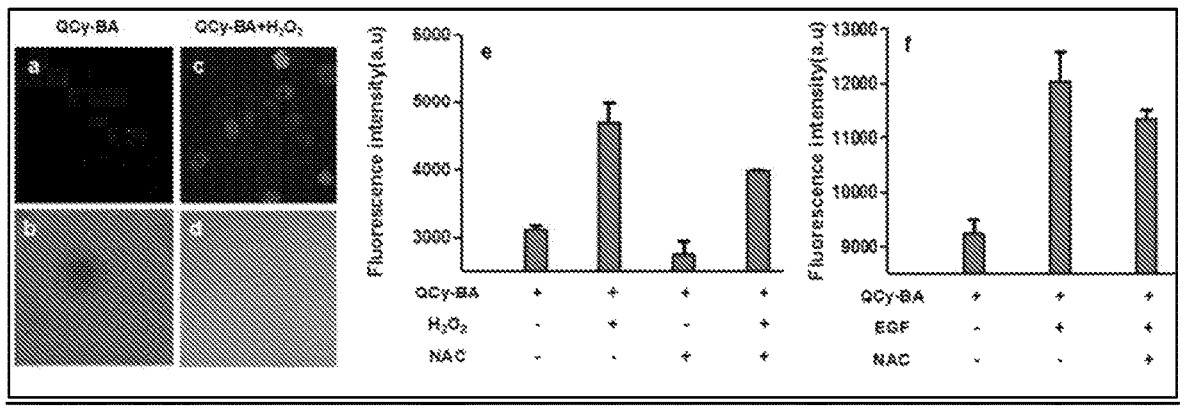

FIG. 4 depicts cellular uptake of QCy-BA and fluorescence reporting of H$_2$O$_2$ in HeLa cells.

FIGS. 4(a) and 4b depict the fluorescence microscope and differential interference contrast (DIC) images of HeLa cells incubated with QCy-BA (5 μM) in the absence of H$_2$O$_2$.

FIGS. 4(c) and 4(d) depict the fluorescence microscope and differential interference contrast (DIC) images of HeLa cells incubated with QCy-BA (5 μM) in the presence of H$_2$O$_2$ (100 μM).

FIGS. 4(e) and 4(f) depict the FACS/flow cytometry analysis showing the PerCP mean fluorescence intensity in HeLa cells. FIG. 4(e) depicts the fluorescence intensity of QCy-BA (5 μM) in HeLa cells upon addition of H$_2$O$_2$ (100 μM) and N-acetyl-L-cysteine (NAC) (8 mM).

FIG. 4(f) depicts the fluorescence intensity of QCy-BA (5 μM) in HeLa cells upon addition of epithelial growth factor (EGF) (500 ng/mL) and N-acetyl-L-cysteine (NAC) (8 mM). Error bars represent ±standard deviation.

Figure 5:
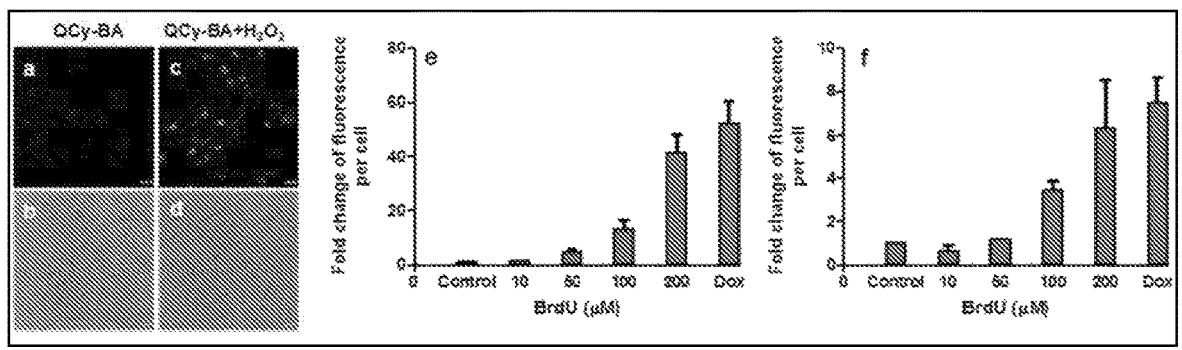

FIG. 5 depicts cellular uptake of QCy-BA in primary MRC5 cells and genotoxic stress-induced H$_2$O$_2$ detection in primary and cancer cells.

FIGS. 5(a) and 5(b) depict the fluorescence microscope and differential interference contrast (DIC) images of MRC5 cells incubated with QCy-BA (5 μM) in the absence of H$_2$O$_2$.

FIGS. 5(c) and 5(d) depict the fluorescence microscope and differential interference contrast (DIC) images of MRC5 cells incubated with QCy-BA (5 μM) in the presence of H$_2$O$_2$ (100 μM).

FIG. 5(e) depicts H$_2$O$_2$ detection in attached live HeLa cells using QCy-BA (5 μM) after treatment with BrdU from 0 to 200 μM or doxorubicin (0.1 μM) for 48 hours. Fold change of fluorescence per cell is normalized to 1 for control cells (n=3).

FIG. 5(f) depicts MRC5 cells treated with BrdU from 0 to 200 μM or doxorubicin (0.1 μM) for 72 hours. H$_2$O$_2$ levels estimated using QCy-BA (5 μM) dye and fold change of fluorescence per cell is normalized to 1 for control cells (n=3).

Figure 6:
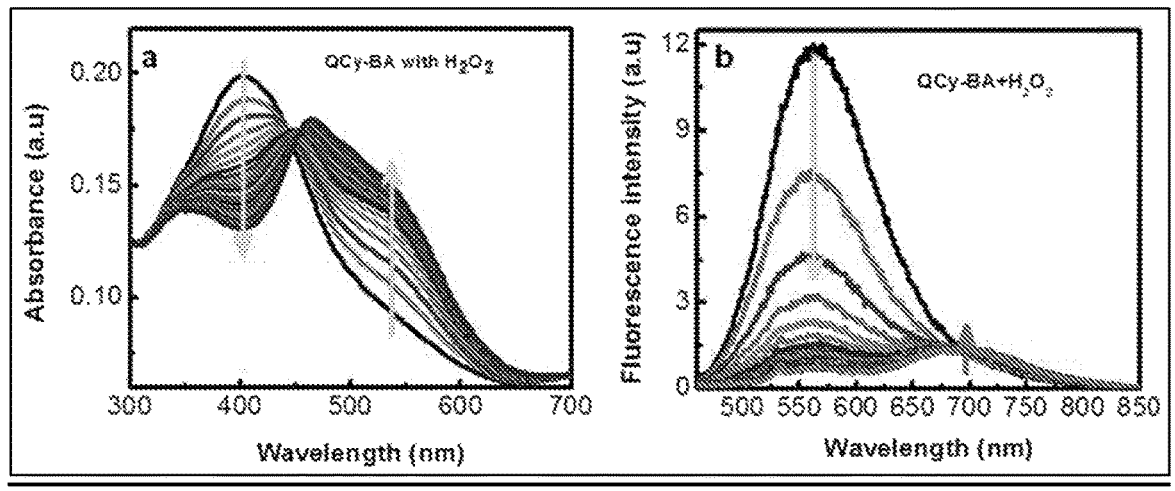

FIG. 6 depicts absorption and emission spectra of QCy-BA, wherein,

FIG. 6(a) depicts the absorption spectra of QCy-BA (5 μM) in presence of H$_2$O$_2$ (1 mM).

FIG. 6(b) depicts the emission spectra of QCy-BA (5 μM) in presence of H$_2$O$_2$ (1 mM) in PBS-buffer solution as a function of time.

Figure 7:
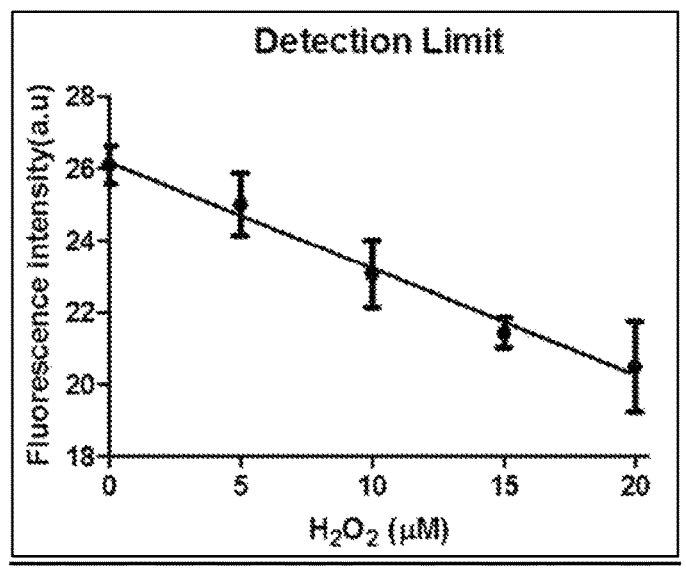

FIG. 7 depicts the plot of the fluorescence intensity at 550 nm against the concentration of [H$_2$O$_2$] PBS-buffer solution. Each data point is acquired after addition of H$_2$O$_2$ at 25° C. The detection limit (5.3 μM) is calculated with 3σ/k; where σ is the standard deviation of blank measurement, k is the slop (−0.30).

Figure 8:
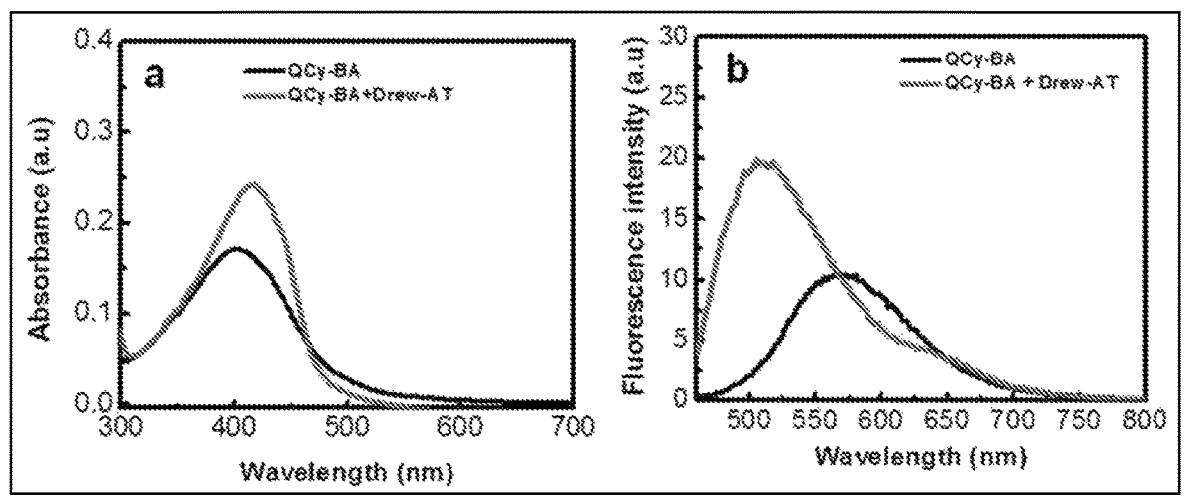

FIG. 8 depicts the absorption and emission spectra of QCy-BA in presence of PBS.

FIG. 8(a) depicts the absorption spectra of QCy-BA (2 μM) in presence of Drew-AT (2 μM).

FIG. 8(b) depicts the emission spectra of QCy-BA (2 μM) in presence of Drew-AT (2 μM) in PBS-buffer solution.

Figure 9:
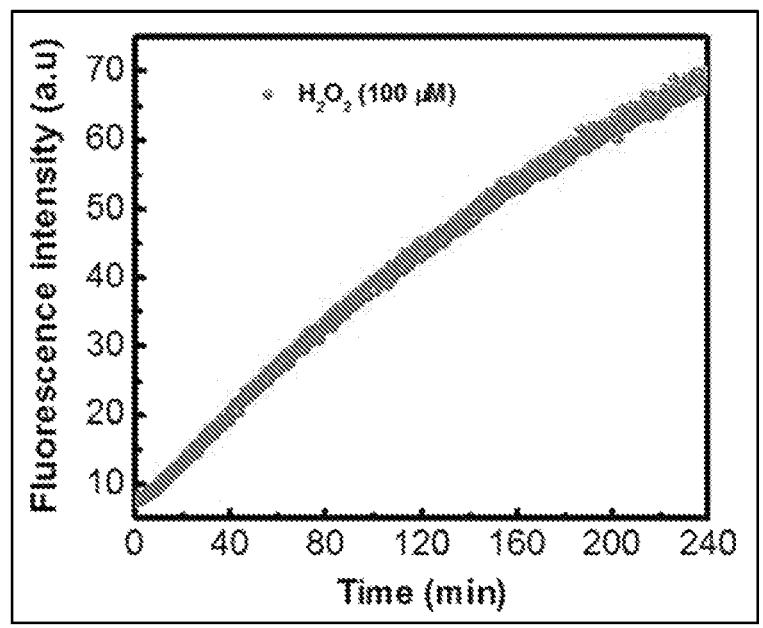

FIG. 9 depicts the time-dependent fluorescence spectra of QCy-BA (2 μM) in presence of Drew-AT (2 μM) after the addition of H$_2$O$_2$ (100 μM) upon excitation at 564 nm.

Figure 10:
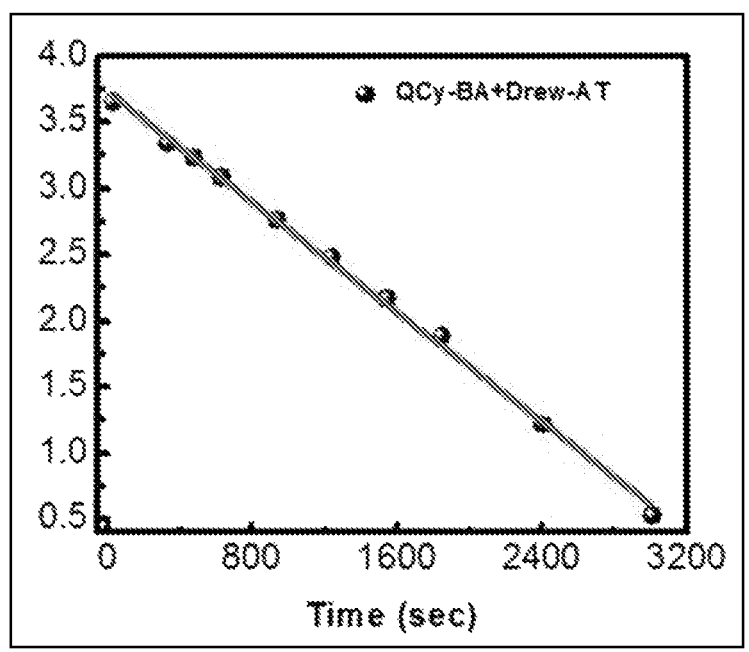

FIG. 10 depicts the plot of ln(F$_\infty$—F) of combination probe QCy-BA ⊂ Drew-AT (2 μM) as a function of time at 650 nm upon addition of H$_2$O$_2$ (1 mM), where F$_\infty$ and F are the fluorescence intensities at 650 nm at time t$_\infty$ (=60 min) and t, respectively. The k$_{obs}$ calculated from the slope of this plot is $1.04 \times 10^{-3}$ s$^{-1}$.

Figure 11:
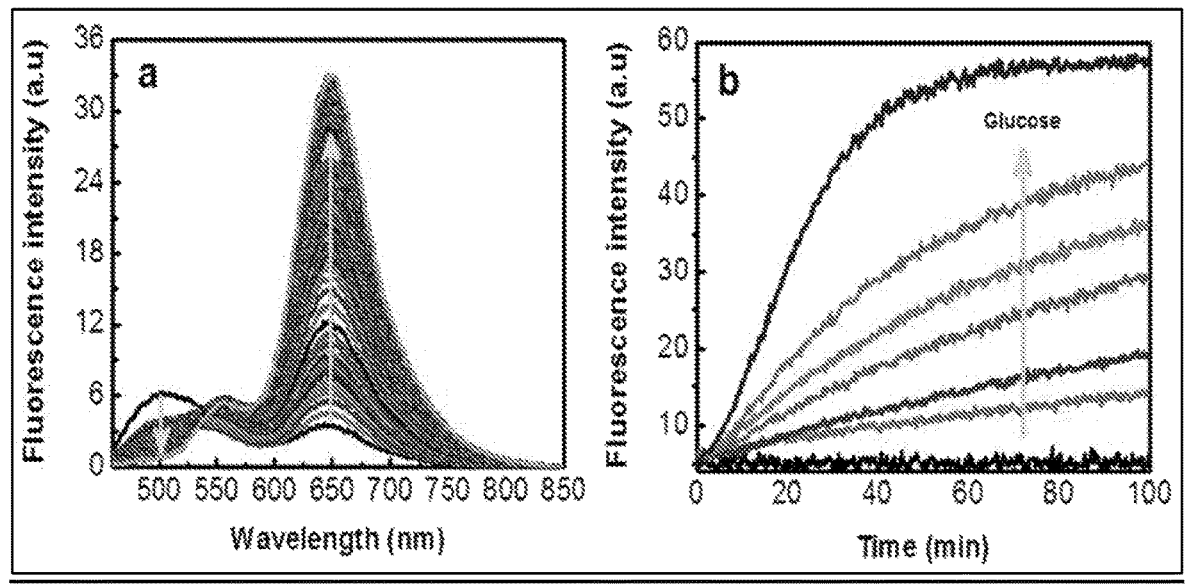

FIG. 11 depicts the fluorescence spectra of combination probe QCy-BA ⊂ Drew-AT.

FIG. 11(a) depicts the fluorescence spectra of combination probe QCy-BA ⊂ Drew-AT in presence of Gox (4 U/mL) and glucose (1 mM) with time, upon excitation at 400 nm.

FIG. 11(b) depicts the plot of fluorescence intensity of combination probe QCy-BA ⊂ Drew-AT at 650 nm as function of time, in presence of Gox (4 U/mL) with increasing concentration of glucose from 0 to 1 mM upon excitation at 564 nm.

Figure 12:
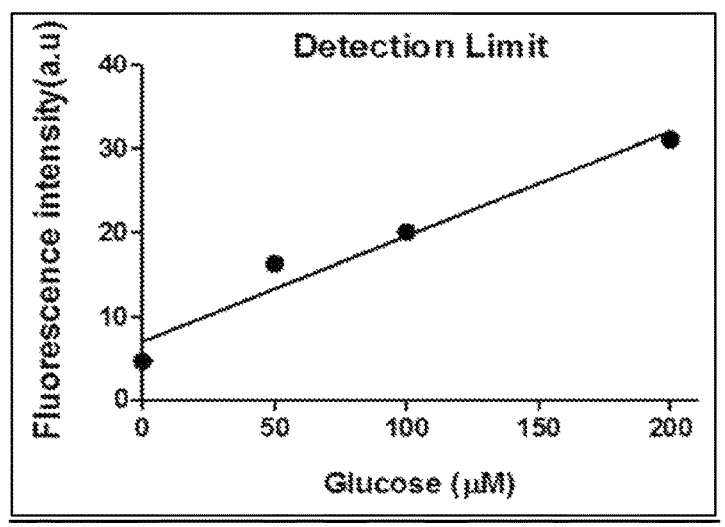

FIG. 12 depicts the plot of fluorescence intensity of combination probe QCy-BA ⊂ Drew-AT in the presence of GOx (4 U/mL) against the concentration of glucose at 650 nm. Each data point is acquired 1 hour after addition of glucose and GOx at 25° C. The detection limit (6.11 μM) is calculated by 3σ/k, where σ is the standard deviation of blank measurement and k is the slop (0.12).

Figure 13:
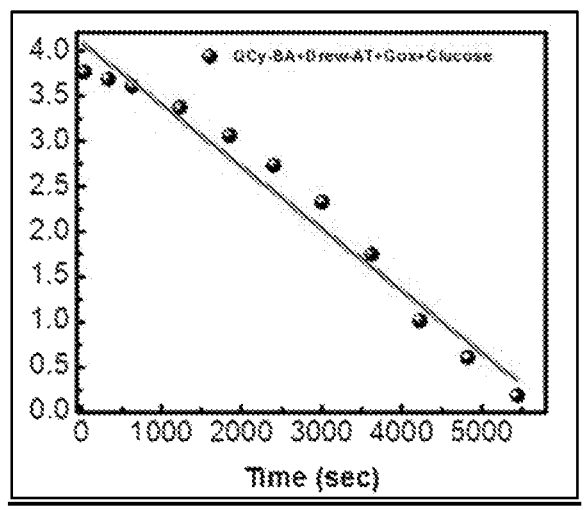

FIG. 13 depicts the plot of ln (F∞—F) of combination probe QCy-BA ⊂ Drew-AT in presence of Gox (4 U/mL) as a function of time at 650 nm upon addition of glucose (1 mM), where F∞ and F are the fluorescence intensities at 650 nm at time $t_\infty$ (=60 min) and t, respectively. The $k_{obs}$ calculated from the slope of this plot is $6.87 \times 10^{-4}$ s$^{-1}$.

Figure 14:
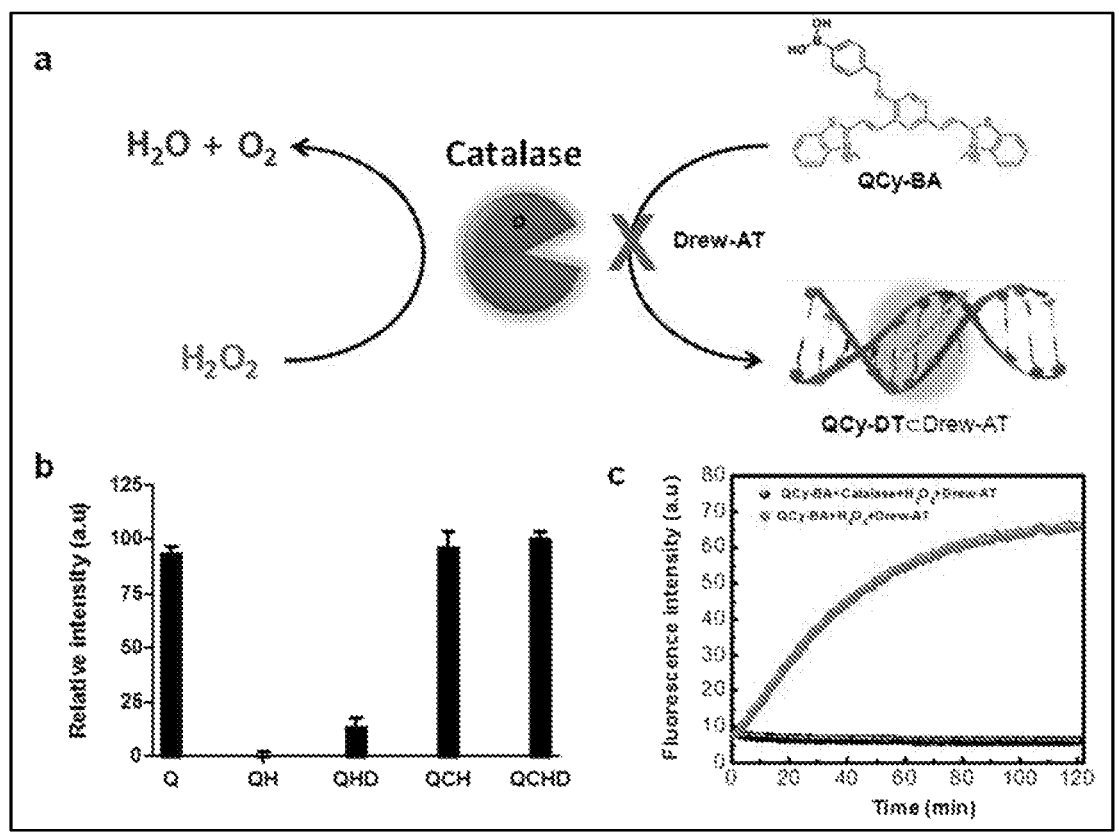

FIG. 14 depicts the study of the combination probe QCy-BA ⊂ Drew-AT under catalase activity.

FIG. 14(a) depicts schematic diagram representing the catalase activity in presence of $H_2O_2$ and combination probe QCy-BA ⊂ Drew-AT.

FIG. 14(b) depicts fluorescence intensity of QCy-BA at 565 nm. Where Q: QCy-BA, QH: QCy–BA+$H_2O_2$, QHD: QCy-BA+$H_2O_2$+Drew–AT, QCH: QCy-BA+Catalase+$H_2O_2$, QCHD: QCy-BA+Catalase+$H_2O_2$+Drew–AT.

FIG. 14(c) depicts time dependent fluorescence of combination probe QCy-BA ⊂ Drew-AT in presence and absence of catalase upon addition of $H_2O_2$ (1 mM) upon excitation at 564 nm.

Figure 15:
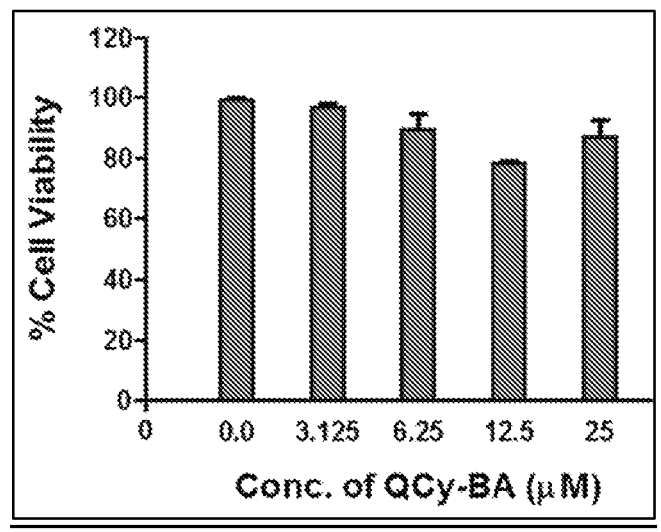

FIG. 15 depicts dose dependent cell viability of HeLa cells by taking 0.0-25 μM of probe QCy-BA for 24 h. Error bars represent ±standard deviation.

Figure 16:
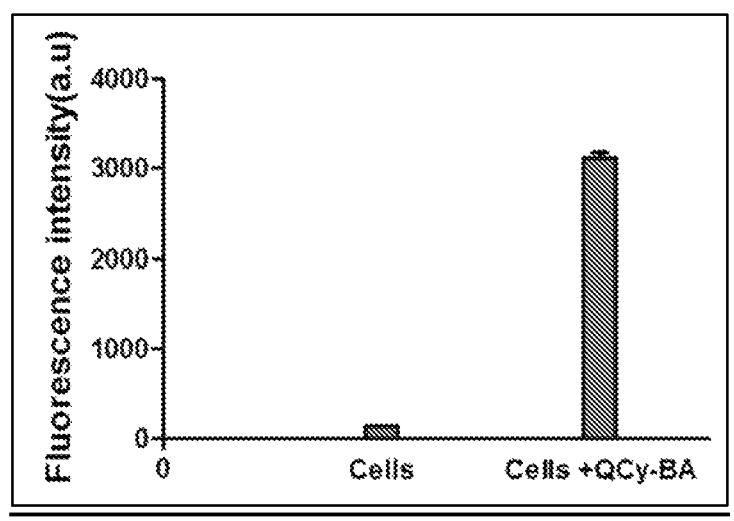

FIG. 16 depicts Flow activated cell sorter (FACS) analysis showing the PerCP mean fluorescence intensity in HeLa cells in presence of QCy-BA (5 μM).

Figure 17:
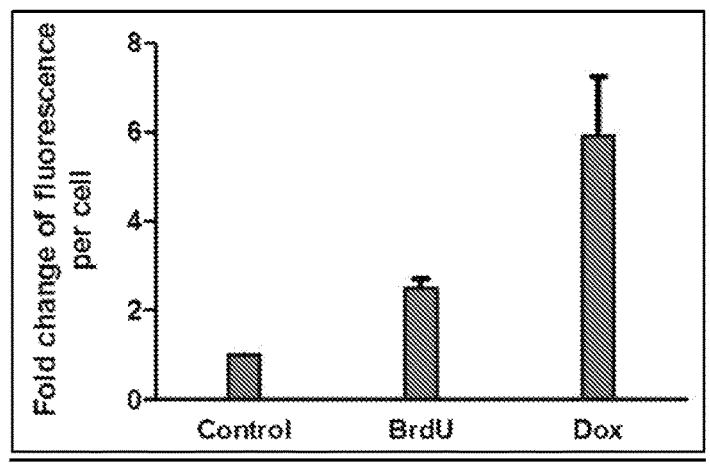

FIG. 17 depicts $H_2O_2$ detection in attached live HeLa cells using DCFDA after treatment with BrdU (100 μM) and doxorubicin (0.1 μM) for 48 h. Fold change of fluorescence per cell is normalized to 1 for control cells (n=3).

Figure 18:
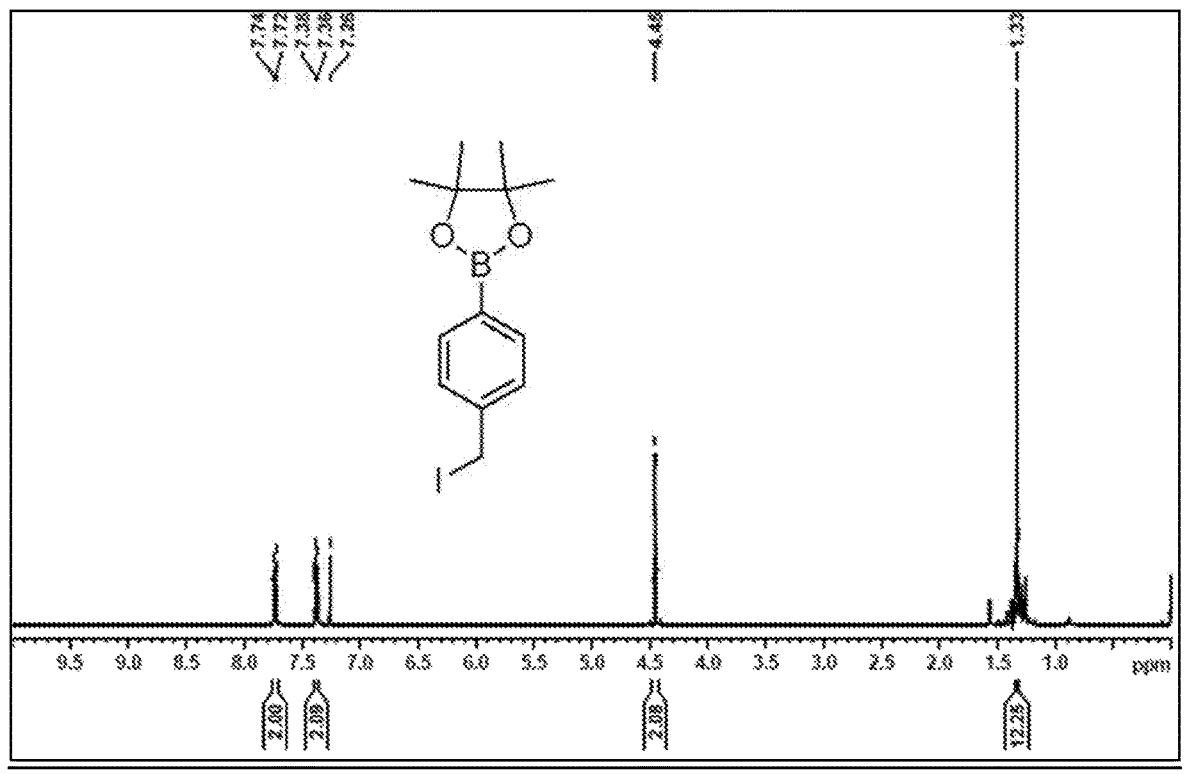

FIG. 18 depicts $^1$HNMR spectrum of compound 2 i.e. 2-(4-(iodomethyl)phenyl)-4,4,5,5-tetramethyl-1,3,2-dioxaborolane.

Figure 19:
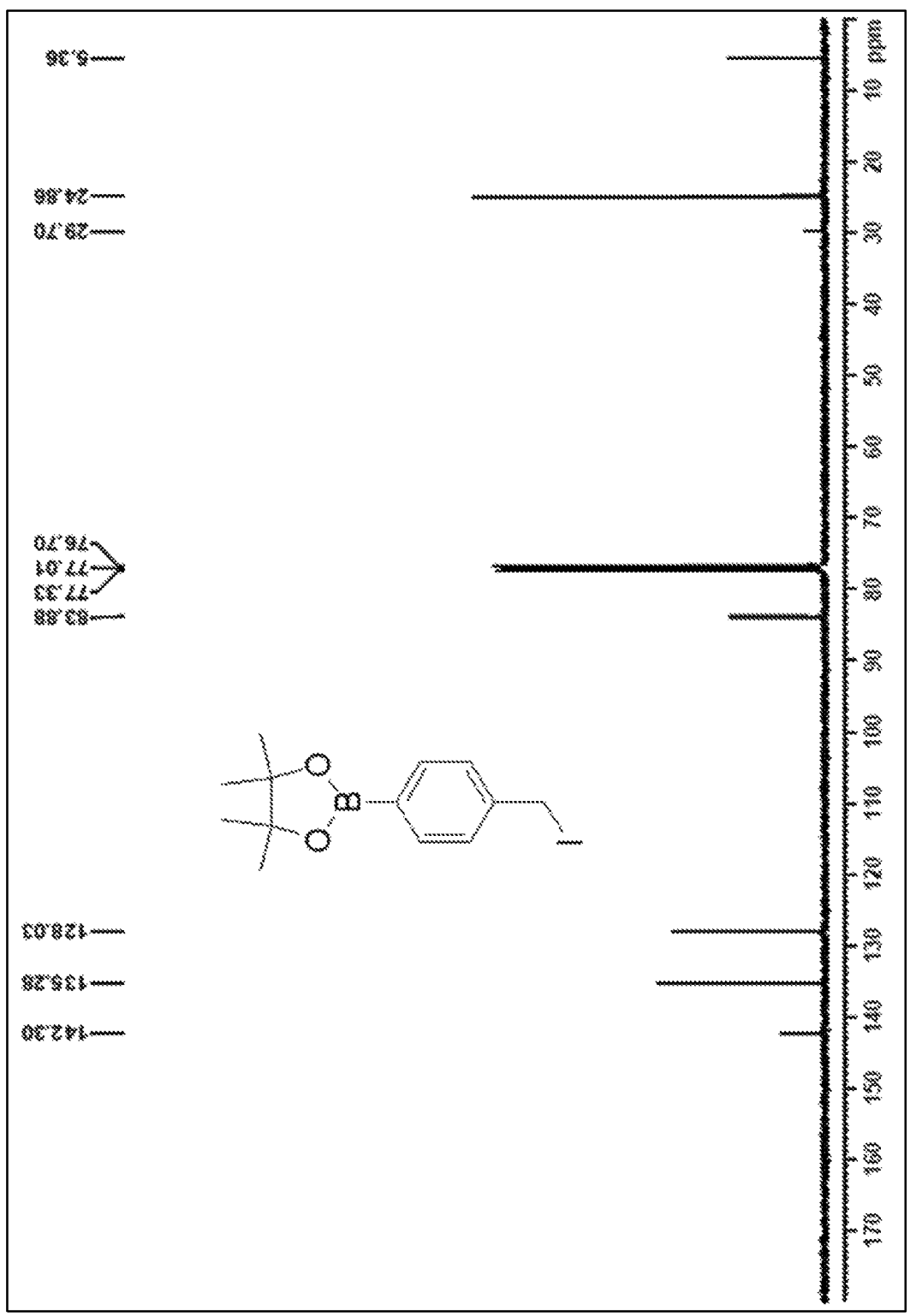

FIG. 19 depicts $^{13}$CNMR spectrum of Compound 2.

Figure 20:
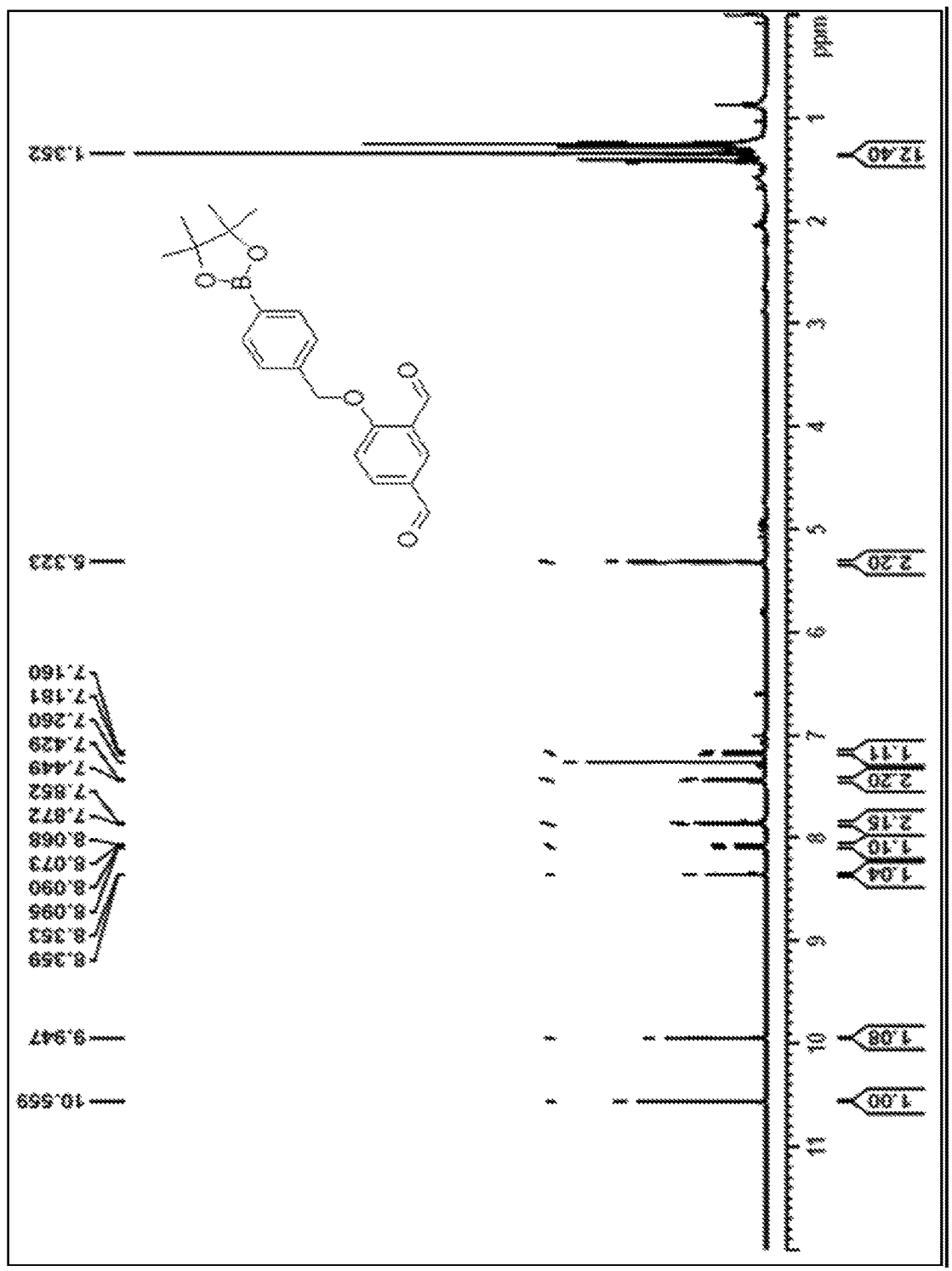

FIG. 20 depicts $^1$HNMR spectrum of Compound 3 i.e. 4-(4-(4,4,5,5-tetramethyl-1,3,2-dioxaborolan-2-yl)benzyloxy)isophthalaldehyde.

Figure 21:
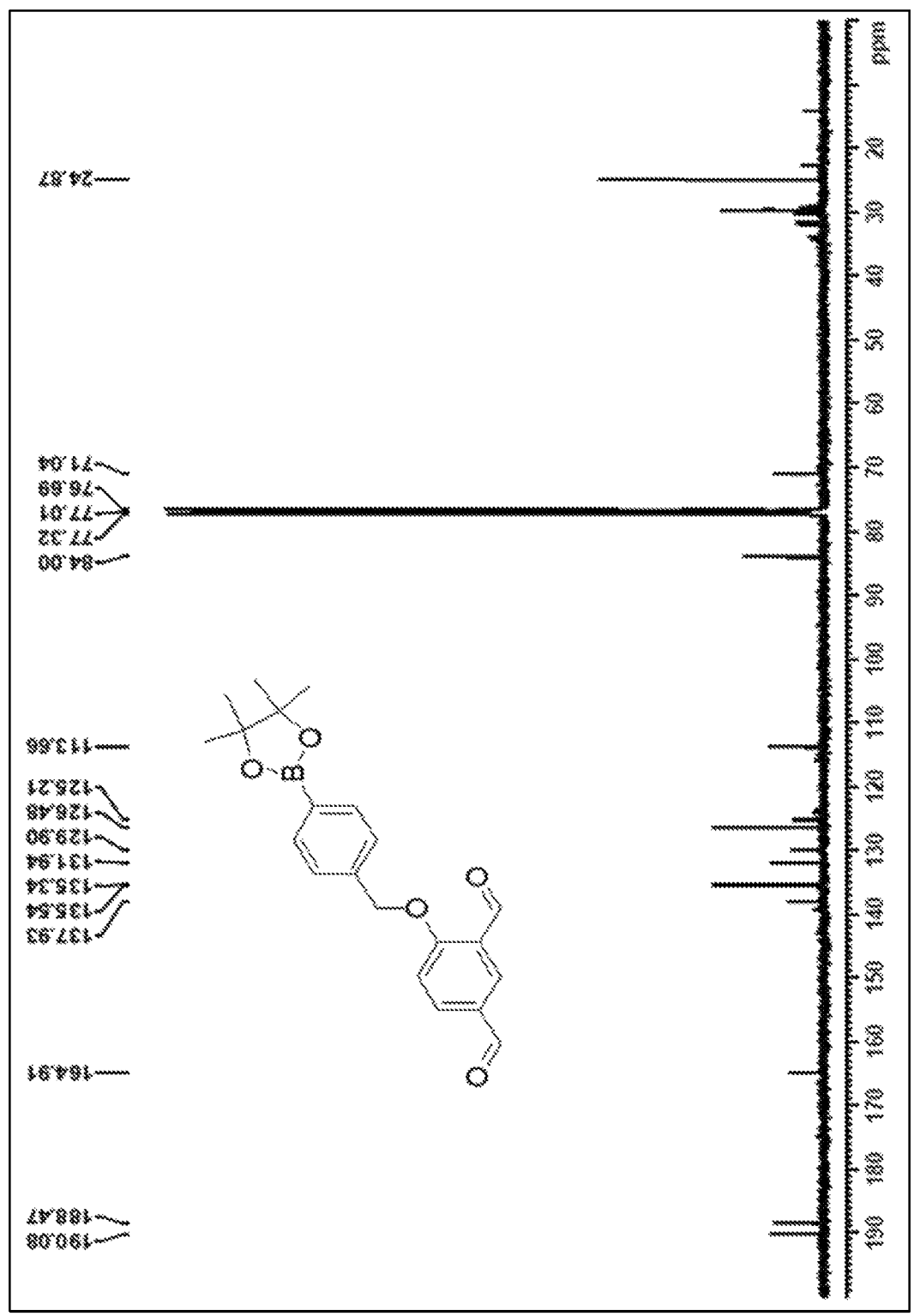
Figure 22:
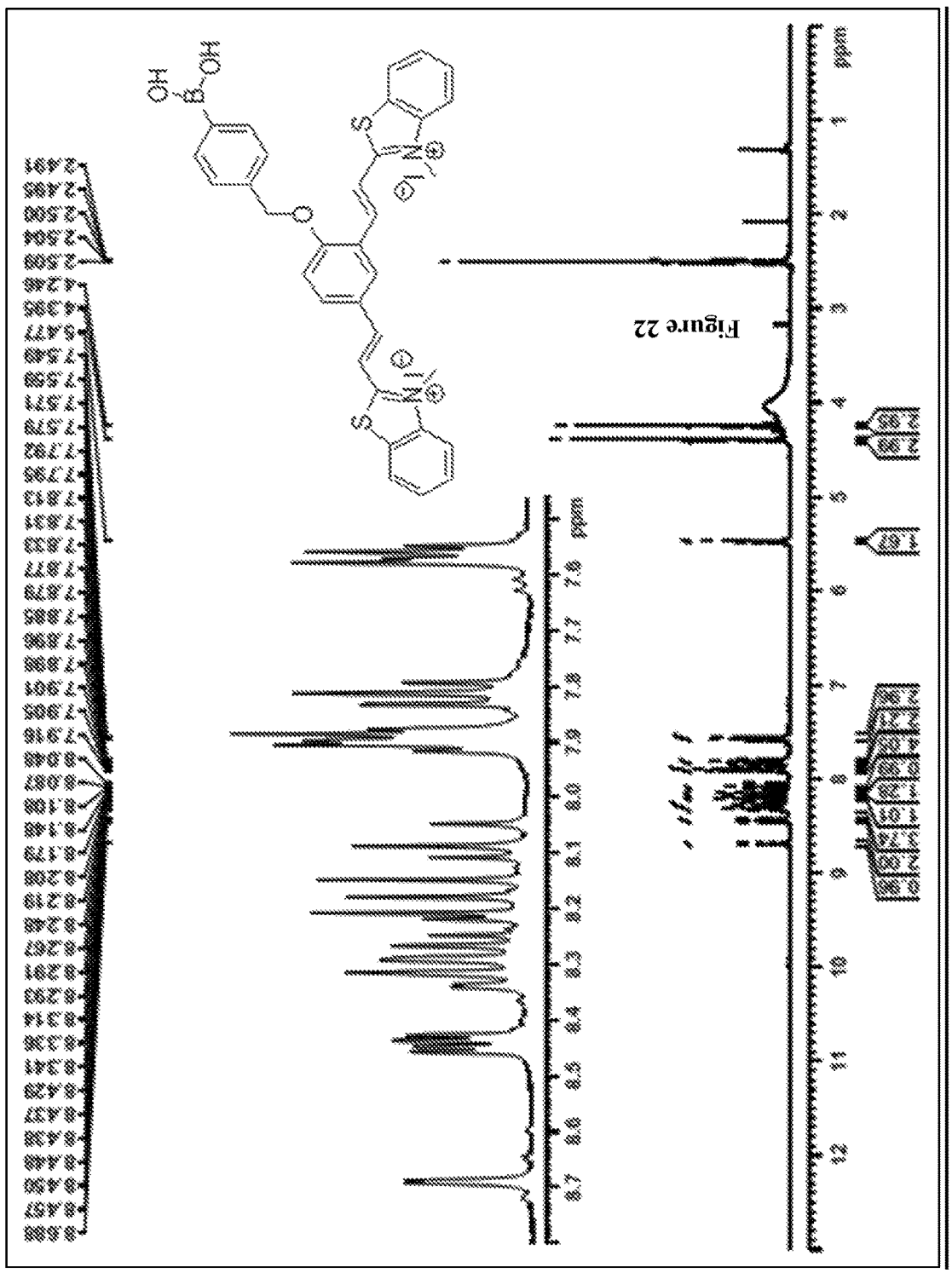
Figure 23:
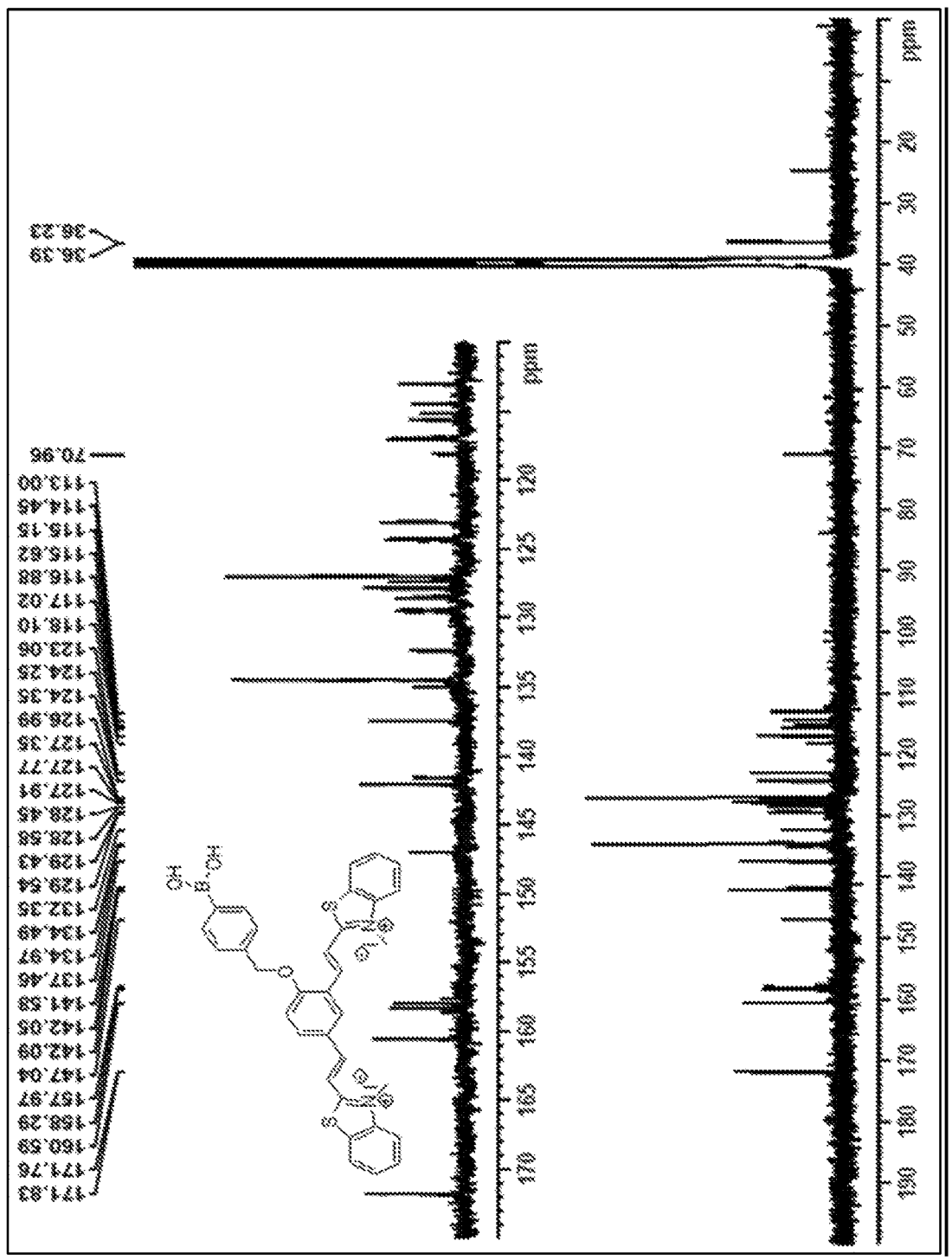
Figure 24:
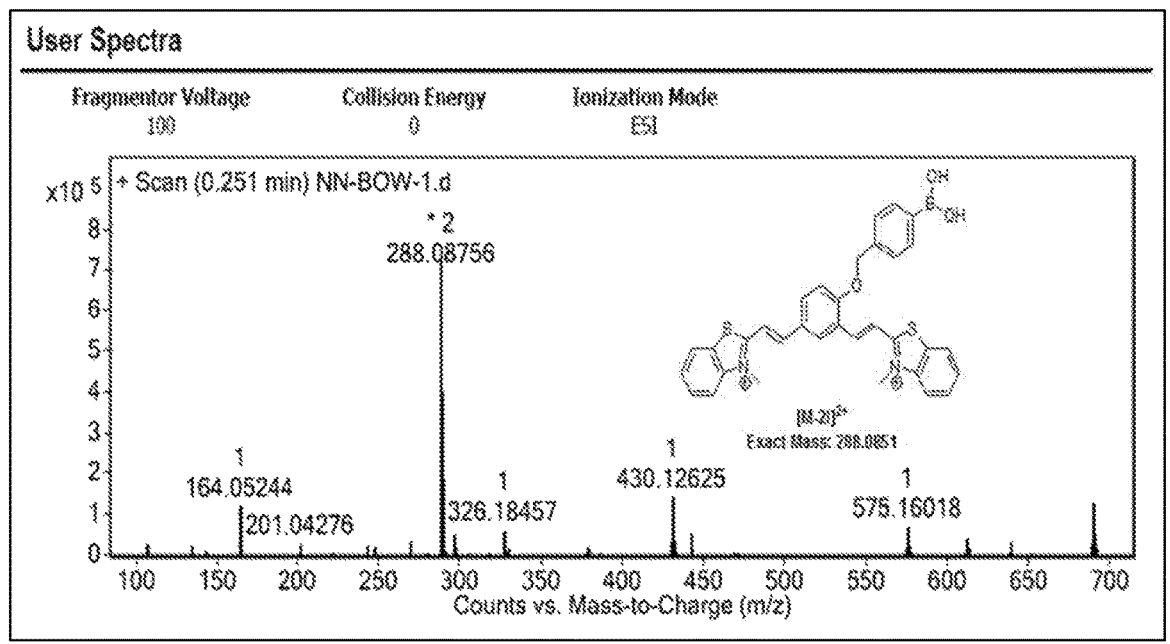
Figure 25:
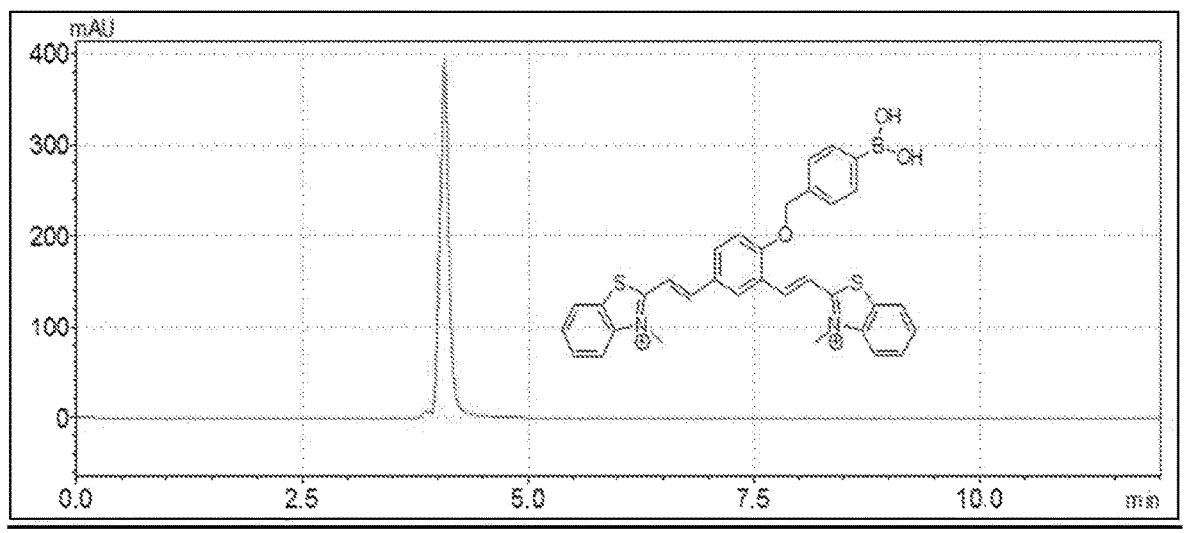

FIG. 21 depicts $^{13}$CNMR spectrum of Compound 3.
FIG. 22 depicts $^1$HNMR spectrum of QCy-BA.
FIG. 23 depicts $^{13}$CNMR spectrum of QCy-BA.
FIG. 24 depicts HRMS mass data of QCy-BA.
FIG. 25 depicts HPLC trace of QCy-BA.

STATEMENT OF THE DISCLOSURE

The present disclosure relates to a compound of Formula I:

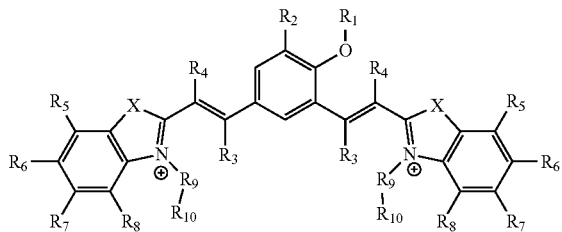

Formula I wherein, 'X' is selected from a group comprising oxygen, sulphur, and selenium;
'$R_1$' is selected from a group comprising alkyl chain, allyl group, aryl group, benzyl group, aryl and alky group, acid, amine, ester, methyl phenyl boronic acid, boronic ester, carbonate, phosphate, silane, quaternary ammonium, amide, imine and any other moiety which can be triggered by chemical or enzymatic tools;
'$R_2$' is selected from a group comprising H, OH, halogen, alkyl and substituted alkyl, and wherein, the halogen is selected from a group comprising bromide, chloride and iodide;
'$R_3$' or '$R_4$' is selected from a group comprising H, alkyl, aryl, nitrile, acid and halogen, and wherein the halogen is selected from a group comprising, chloride, fluoride, bromide and iodide;
'$R_5$', '$R_6$', '$R_7$' or '$R_8$' is selected from a group comprising H, OH, alkyl, aryl, halogen, nitro, sulfonates ($SO_3^-$) and nitrile group;
'$R_9$' is selected from a group comprising H and —$(CH_2)_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$);
or its salt, derivative, tautomer, isomer, polymorph, analog, solvate or intermediate thereof;
a process for preparation of compound of Formula I:

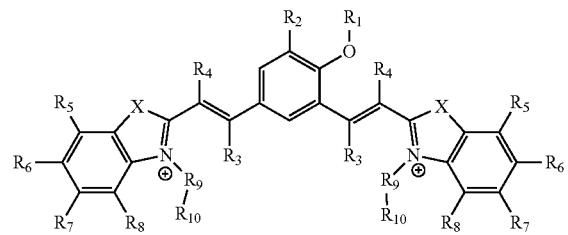

Formula I wherein, 'X' is selected from a group comprising oxygen, sulphur, and selenium;
'$R_1$' is selected from a group comprising alkyl chain, allyl group, aryl group, benzyl group, aryl and alky group, acid, amine, ester, methyl phenyl boronic acid, boronic ester, carbonate, phosphate, silane, quaternary ammonium, amide, imine and any other moiety which can be triggered by chemical and enzymatic tools;
'$R_2$' is selected from a group comprising H, OH, halogen, alkyl and substituted alkyl, and wherein, the halogen is selected from a group comprising bromide, chloride and iodide;
'$R_3$' or '$R_4$' is selected from a group comprising H, alkyl, aryl, nitrile, acid and halogen, and wherein the halogen is selected from a group comprising, chloride, fluoride, bromide and iodide;
'$R_5$', '$R_6$', '$R_7$' or '$R_8$' is selected from a group compris-ing H, OH, alkyl, aryl, halogen, nitro, sulfonates ($SO_3^-$) and nitrile group;
'$R_9$' is selected from a group comprising H and —$(CH_2)_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$);
or its salt, derivative, tautomeric form, isomer, polymorph, analog, solvate or intermediates thereof;
said process comprising:
a. reacting compound of Formula II with compound of Formula III to obtain compound of Formula IV

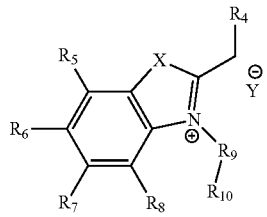

Formula IV

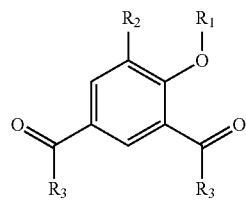

Formula V wherein,
'R$_4$' is selected from a group comprising H, alkyl, aryl, nitrile, acid and halogen, and wherein the halogen is selected from a group comprising, chloride, fluoride, bromide and iodide;

'R$_5$', 'R$_6$', 'R$_7$' or 'R$_8$' is selected from a group comprising H, OH, alkyl, aryl, halogen, nitro, sulfonates (SO$_3^-$) and nitrile group;

'R$_9$' is selected from a group comprising H and —(CH$_2$)$_n$—, wherein 'n' is 1-6; and 'R$_{10}$' is selected from a group comprising hydrogen, —OH, methyl, amine, terminal alkyne, alkene, alkyl acid, amine acid and sulfonates (SO$_3^-$);

'Y' is either Br or I;

wherein,
'R$_1$' is hydrogen;
'R$_2$' is selected from a group comprising H, OH, halogen, alkyl and substituted alkyl, and wherein, the halogen is selected from a group comprising bromide, chloride and iodide; and
'R$_3$' is selected from a group comprising H, alkyl, aryl, nitrile, acid and halogen, and wherein the halogen is selected from a group comprising, chloride, fluoride, bromide and iodide;

a compound of Formula I as described above selected from

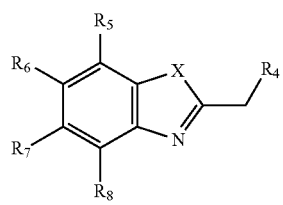

Formula II wherein,
'R$_4$' is selected from a group comprising H, alkyl, aryl, nitrile, acid and halogen, and wherein the halogen is selected from a group comprising, chloride, fluoride, bromide and iodide; and 'R$_5$', 'R$_6$', 'R$_7$' or 'R$_8$' is selected from a group comprising H, OH, alkyl, aryl, halogen, nitro, sulfonates (SO$_3^-$) and nitrile group;

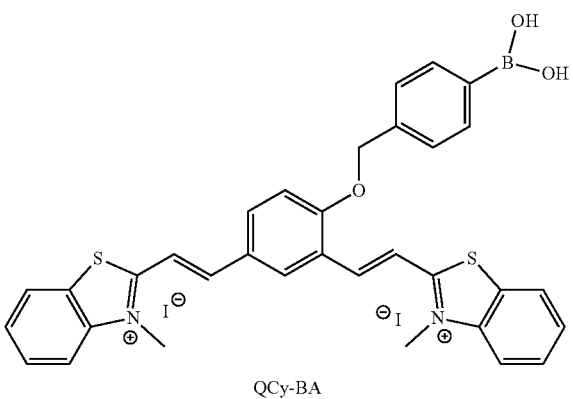

QCy-BA

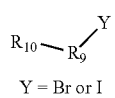

Formula III

Y = Br or I wherein,
'R$_9$' is selected from a group comprising H and —(CH$_2$)$_n$—, wherein 'n' is 1-6;
'R$_{10}$' is selected from a group comprising hydrogen, —OH, methyl, amine, terminal alkyne, alkene, alkyl acid, amine acid and sulfonates (SO$_3^-$); and, b. reacting the compound of Formula IV with compound of Formula V in presence of piperidine and alcohol.

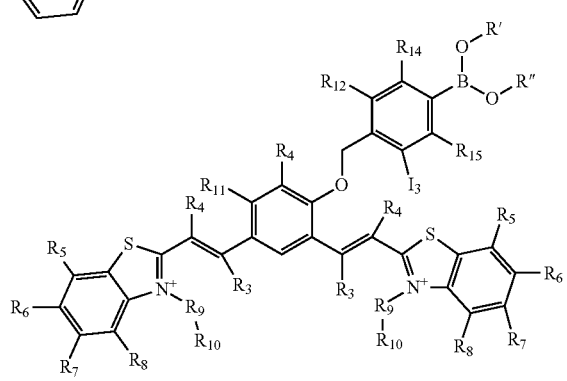

-continued

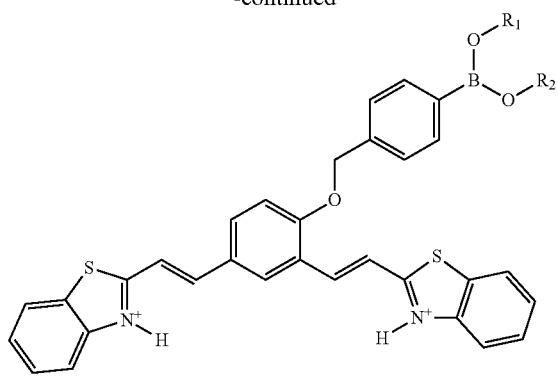

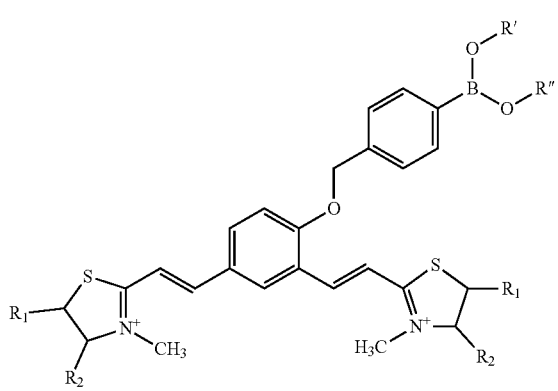

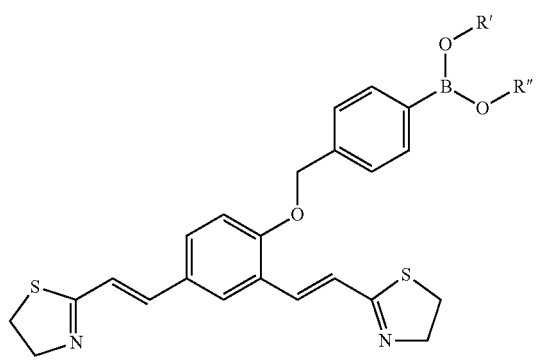

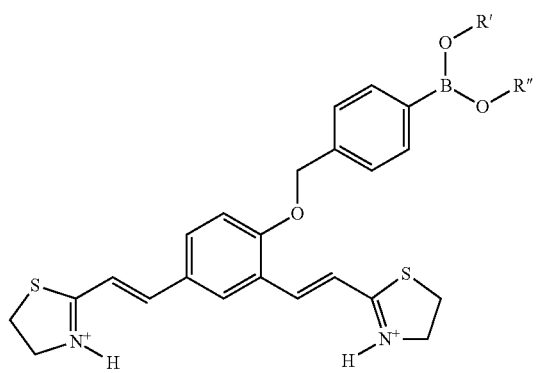

-continued

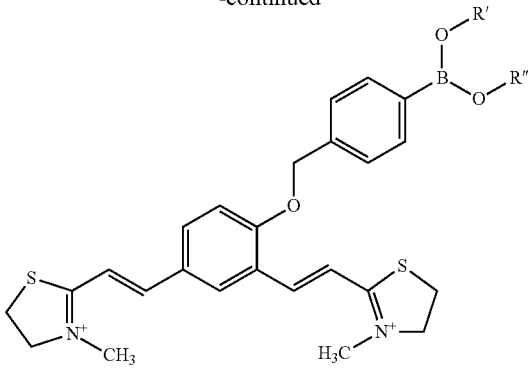

$R_1$ to $R_{14}$ or R' and R" are independently selected from a group comprising alkyl, aryl, alicyclic, heterocyclic, hetero atom selected from a group comprising O, N, P, S, halogens, cyclic, acyclic ring system;

a pharmaceutical composition comprising the compound of Formula I its salt, derivative, tautomeric form, isomer, polymorph, analog, solvate and intermediates thereof, optionally along with at least one pharmaceutically acceptable excipient;

a method of detecting or quantifying the presence of reactive oxygen species (ROS) in a biological sample, said method comprising the act of contacting the compound of Formula I or its salt, derivative, tautomer, isomer, polymorph, analog, solvate or intermediates thereof, or the composition of claim 8 with the sample and detecting the fluorescence indicative of the presence of ROS in the biological sample;

a method for detecting or quantifying a ROS compound in vivo in a subject, said method comprising:
  a. administering to a subject, a compound of Formula 1;
  b. allowing said compound of Formula 1 to react with a ROS; and
  c. detecting or quantifying the fluorescence, indicative of the presence of ROS compound in vivo;

a method of diagnosing a disease condition in a subject, said method comprising contacting the compound of Formula I or its salt, derivative, tautomer, isomer, polymorph, analog, solvate or intermediates thereof, or the composition of comprising compound of formula I with a sample obtained from the subject;

a method of inhibiting growth of a cell, said method comprising contacting the compound of Formula I or its salt, derivative, tautomer, isomer, polymorph, analog, solvate or intermediates thereof, the composition comprising compound of formula I with the cell;

a method of treating a disease characterized by abnormal levels of ROS in a subject, said method comprising step of administering the compound of Formula I or its salt, derivative, tautomer, isomer, polymorph, analog, solvate or its intermediates thereof, or the composition comprising compound of formula I in said subject to treat the disease; and a kit for detecting reactive oxygen species (ROS) in a sample, wherein the kit comprising the compound of formula I or its salt, derivative, tautomer, isomer, polymorph, analog, solvate or intermediates thereof; or a composition comprising compound of formula I, wherein the said compound is present in an amount effective to detect the presence of ROS.

DETAILED DESCRIPTION OF THE DISCLOSURE

The present disclosure relates to a compound of Formula I:

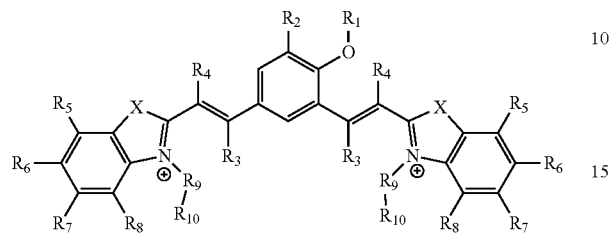

Formula I wherein,
- 'X' is selected from a group comprising oxygen, sulphur, and selenium;
- '$R_1$' is selected from a group comprising alkyl chain, allyl group, aryl group, benzyl group, aryl and alky group, acid, amine, ester, methyl phenyl boronic acid, boronic ester, carbonate, phosphate, silane, quaternary ammonium, amide, imine and any other moiety which can be triggered by chemical or enzymatic tools;
- '$R_2$' is selected from a group comprising H, OH, halogen, alkyl and substituted alkyl, and wherein, the halogen is selected from a group comprising bromide, chloride and iodide;
- '$R_3$' or '$R_4$' is selected from a group comprising H, alkyl, aryl, nitrile, acid and halogen, and wherein the halogen is selected from a group comprising, chloride, fluoride, bromide and iodide;
- '$R_5$', '$R_6$', '$R_7$' or '$R_8$' is selected from a group comprising H, OH, alkyl, aryl, halogen, nitro, sulfonates ($SO_3^-$) and nitrile group;
- '$R_9$' is selected from a group comprising H and —$(CH_2)_n$—, wherein 'n' is 1-6;
- '$R_{10}$' is selected from a group comprising hydrogen, —OH, methyl, amine, terminal alkyne, alkene, alkyl acid, amine acid and sulfonates ($SO_3^-$).

In an embodiment of the present disclosure, the compound of Formula I includes but is not limited to 4-((N, N-dimethyl, 2,4-bis((E)-2-(benzo[d]thiazol-2-ylinium) vinyl) phenoxy) methyl) phenylboronic acid.

In another embodiment, the structure of 4-((N, N-dimethyl, 2,4-bis((E)-2-(benzo[d]thiazol-2-ylinium)vinyl)phenoxy)methyl)phenylboronic acid (QCy-BA) is provided below:

In yet another embodiment of the present disclosure, compound of Formula I is selected from

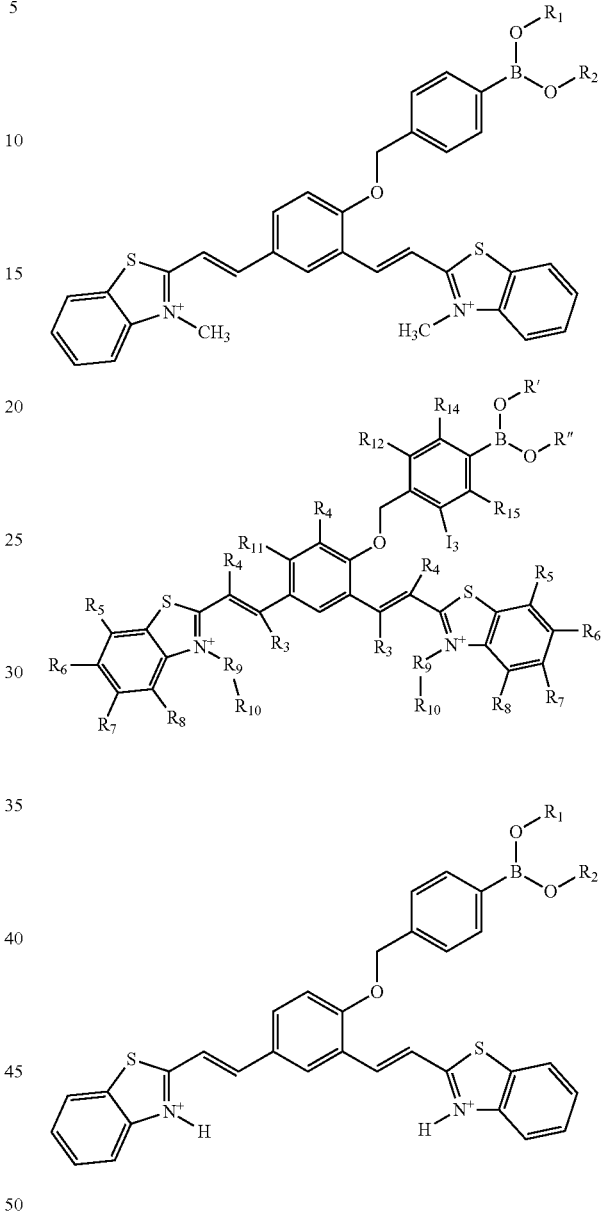

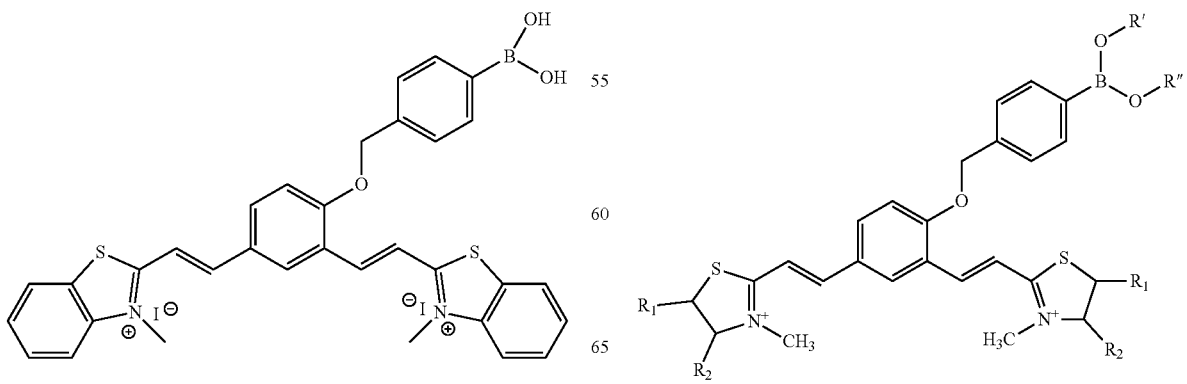

-continued

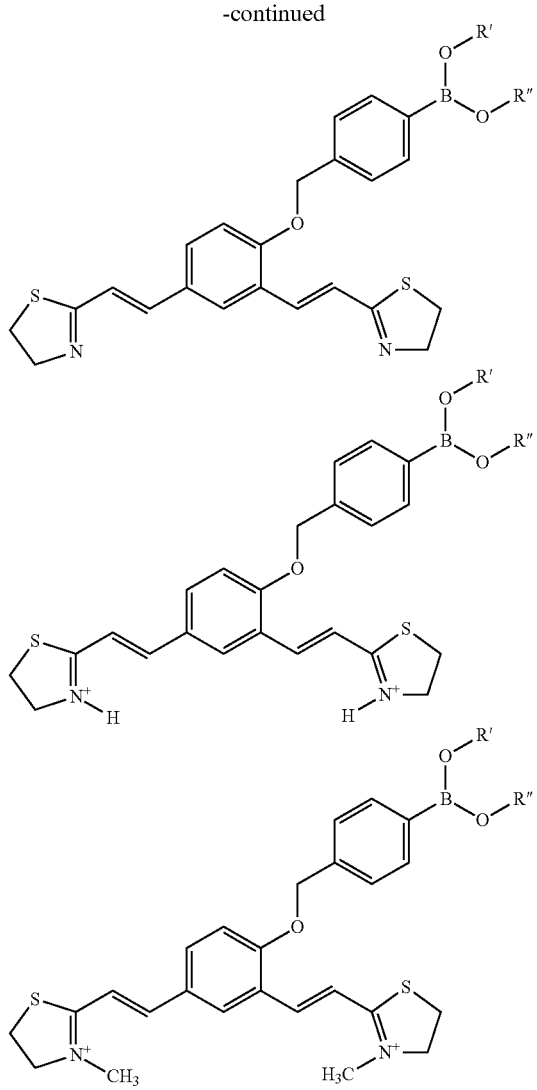

R₁ to R₁₄ or R' and R" are independently selected from a group comprising alkyl, aryl, alicyclic, heterocyclic, hetero atom selected from a group comprising O, N, P, S, halogens, cyclic, acyclic ring system;

In an embodiment of the present disclosure, tautomers, isomers, analogs, derivatives and salts of Formula I compounds are also provided.

The present disclosure relates to compound of Formula I which is a probe and is specific or selective to reactive oxygen species. In an exemplary embodiment, the Formula I compound QCy-BA is specific or selective to $H_2O_2$.

In another embodiment of the present disclosure, Formula I compounds, particularly compounds with aryl boronates (R₁) are unique chemical moieties with selective reactivity towards the amphiphilic $H_2O_2$, a desirable property to achieve specificity and selectivity over other biologically relevant reactive oxidative species (ROS).

In yet another embodiment, initially, the boronate functionality in Formula I acts as an electrophilic center and reacts with the nucleophile to generate the tetrahedral-boronate complex. Subsequently, the carbon-boron (C—B) bond becomes labile and acts as a nucleophile towards the electrophilic oxygen center of $H_2O_2$. In particular, the aryl boronate functionality becomes a specific reorganization center for $H_2O_2$ among all other biological oxygen metabolites and ROS, which operate through one electron transfer or electrophilic oxidation pathways.

In an embodiment, the Formula I compound QCy-BA is QCy-DT compound (a DNA minor groove binder) functionalized with methyl phenyl boronic acid. QCy-BA possesses two positively charged nitrogen atom-containing benzothiazoles, with distinct conjugation patterns around the central phenolic moiety derivatized with phenylboronic acid functionality. Furthermore, the electron delocalization in QCy-BA is disrupted as a consequence of masking the central phenolic hydroxyl with phenyl boronic acid functionality. Upon slicing of the phenyl boronic acid functionality in response to the $H_2O_2$ stimulus, QCy-BA transforms into the negatively charged phenolate of QCy-DT. The generation of phenolate restores the electron transfer towards one of the positively charged nitrogen atoms of the benzothiazole accepter. This restores internal charge transfer (ICT) to generate a highly electron delocalized π-system with NIR-fluorescence in the presence of DNA (as shown in FIG. 1(a)).

In another embodiment, Formula I compounds, particularly, phenyl boronic acid-functionalized quinone-cyanine (QCy-BA) in combination with AT-rich DNA (Drew-AT), i.e., QCy-BA⊂Drew-AT as a stimuli-responsive NIR fluorescence probe for in vitro levels of $H_2O_2$ is presented. In response to cellular $H_2O_2$ stimulus, QCy-BA converts into QCy-DT, a one-donor-two-acceptor (D2A) system that exhibits switch-on NIR florescence upon binding to DNA minor groove. Fluorescence studies on combination probe QCy-BA⊂Drew-AT show strong NIR fluorescence selectively in the presence of $H_2O_2$. Further, glucose oxidase (Gox) assay confirms that the combination probe QCy-BA⊂Drew-AT is highly efficient for probing $H_2O_2$ generated in situ through Gox-mediated glucose oxidation. Quantitative analysis through fluorescence plate reader, flow cytometry and live imaging approaches show that the Formula I compounds including QCy-BA is a promising probe to detect normal as well as elevated levels of $H_2O_2$ produced by EGF/Nox pathways and post-genotoxic stress in primary cells as well as senescent cells. Thus, the Formula I compounds including QCy-BA, in combination with exogenous or cellular DNA are versatile probes to quantify and image $H_2O_2$ in normal and disease-related cells.

In an embodiment, the phrase AT-rich DNA refers to DNA which consists more percentage of AT-base pairs than GC-base pairs.

In another embodiment, functionalization of the compounds of Formula I (such as QCy-BA) with a stimuli-responsive appendage ($H_2O_2$) is a promising and efficient method to in situ generate the active probe (QCy-DT) in response to $H_2O_2$. Such a probe with signal capturing and amplification assisted by an additional recognition event, DNA-binding in the present disclosure, is highly advantageous for probing specific biological activity in a cellular environment.

Structurally, QCy-DT has a free hydroxyl group readily available for functionalization with a large number of chemically or enzymatically cleavable appendages to make it a versatile and promising stimuli-responsive probe.

In another embodiment, the probe QCy-BA in response to specific stimulus (chemical or enzyme), is cleaved to release an NIR-fluorescence ready QCy-DT probe, which upon binding the minor grove of DNA fluoresces strongly, thus, aiding the imaging and quantification of the stimulus.

In another embodiment, the probe QCy-BA acts as a stimulus receiver or protectant and upon sensing the stimulus gets converted to the activated dye/probe QCy-DT in order to bind to the minor grove of the DNA.

In another embodiment, functionalizing the DNA binding fluorescence probe QCy-DT with aryl boronates is an attractive strategy for the development of a stimuli-responsive fluorescence probe (Formula I compounds) for $H_2O_2$. Accordingly, QCy-DT hydroxyl group is functionalized to obtain methyl phenyl boronic acid (QCy-BA, FIG. 1(a)), which reacts selectively with $H_2O_2$ to release the parent DNA binding dye. In another embodiment, phenyl boronate is the preferred appendage owing to the fact that the reaction between $H_2O_2$ and boronic acid or ester is highly chemospecific, bioorthogonal and biocompatible while the byproducts are non-toxic to living cells.

In an exemplary embodiment, methyl phenyl boronic acid conjugated one-donor-two-acceptor (D2A) π-electron-based quinone-cyanine (QCy-BA) moiety is provided, which in combination with AT-rich DNA (such as Drew-AT) acts as a stimuli-responsive NIR fluorescence probe for $H_2O_2$ (FIG. 1(a)). The major advantage with NIR fluorescence combination probe is that it circumvents the false positive results by means of a double check on the signal outcome and background fluorescence from in vitro and in vivo studies. In the presence of $H_2O_2$, QCy-BA releases non-fluorescent QCy-DT, which upon binding AT-rich DNA shows enhanced fluorescence in the NIR region. Nuclear magnetic resonance (NMR) and UV-vis absorption studies reveal the efficient conversion of QCy-BA to QCy-DT and p-quinonemethide through selective 1,6-elimination rearrangement in the presence of $H_2O_2$ over other ROS (FIG. 1(a)). Fluorescence studies of QCy-BA show strong NIR fluorescence enhancement in the presence of $H_2O_2$ and AT-rich DNA (Drew-AT), which clearly endorses the use of combination probes such as QCy-BA ⊂ Drew-AT for the fluorometric detection of $H_2O_2$ ratiometrically. Glucose oxidase assay confirm that the combination probe QCy-BA ⊂ Drew-AT is capable of monitoring in situ generated $H_2O_2$ by the oxidation of glucose using glucose oxidase (GOx). Live cell imaging studies show the staining of cell nucleus by the in situ generated NIR fluorescence-ready probe in the presence of $H_2O_2$. Fluorescence activated cell sorting (FACS) analysis show that probe QCy-BA is equally efficient in detecting the normal and in situ generated $H_2O_2$ in response to Nox-mediated growth factor signaling pathways. Further, probe QCy-BA is capable of detecting elevated levels of $H_2O_2$ generated either through insult by doxorubicin (Dox) or 5-bromo-2'-deoxyuridine (BrdU) in primary or cancer cells, which results in the induction of cellular senescence. Therefore, Formula I compounds such as probe QCy-BA in combination with exogenous or cellular DNA is a promising stimuli-responsive NIR fluorescence combination probe for investigating $H_2O_2$ production and concentration levels in living cells, which can further assist the imaging and diagnosis of disease-related cells.

The present disclosure also relates to a process for preparation of compound of Formula I:

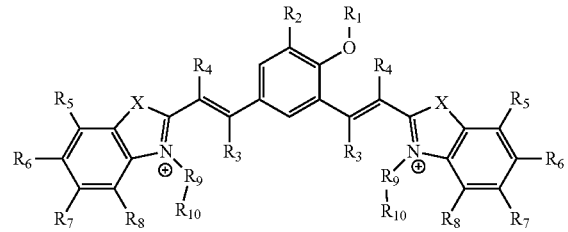

Formula I wherein, 'X' is selected from a group comprising oxygen, sulphur, and selenium;
'$R_1$' is selected from a group comprising alkyl chain, allyl group, aryl group, benzyl group, aryl and alky group, acid, amine, ester, methyl phenyl boronic acid, boronic ester, carbonate, phosphate, silane, quaternary ammonium, amide, imine and any other moiety which can be triggered by chemical and enzymatic tools;
'$R_2$' is selected from a group comprising H, OH, halogen, alkyl and substituted alkyl, and wherein, the halogen is selected from a group comprising bromide, chloride and iodide;
'$R_3$' or '$R_4$' is selected from a group comprising H, alkyl, aryl, nitrile, acid and halogen, and wherein the halogen is selected from a group comprising, chloride, fluoride, bromide and iodide;
'$R_5$', '$R_6$', '$R_7$' or '$R_8$' is selected from a group comprising H, OH, alkyl, aryl, halogen, nitro, sulfonates ($SO_3^-$) and nitrile group;
'$R_9$' is selected from a group comprising H and —$(CH_2)_n$—, wherein 'n' is 1-6;
'$R_{10}$' is selected from a group comprising hydrogen, —OH, methyl, amine, terminal alkyne, alkene, alkyl acid, amine acid and sulfonates ($SO_3^-$);
or its salt, derivative, tautomeric form, isomer, polymorph, analog, solvate and intermediates thereof;
said process comprising:
b. reacting compound of Formula II with compound of Formula III to obtain compound of Formula IV

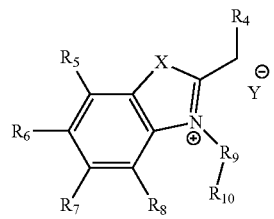

Formula IV wherein,
'$R_4$' is selected from a group comprising H, alkyl, aryl, nitrile, acid and halogen, and wherein the halogen is selected from a group comprising, chloride, fluoride, bromide and iodide;

'R$_5$', 'R$_6$', 'R$_7$' or 'R$_8$' is selected from a group comprising H, OH, alkyl, aryl, halogen, nitro, sulfonates (SO$_3^-$) and nitrile group;

'R$_9$' is selected from a group comprising H and —(CH$_2$)$_n$—, wherein 'n' is 1-6; and 'R$_{10}$' is selected from a group comprising hydrogen, —OH, methyl, amine, terminal alkyne, alkene, alkyl acid, amine acid and sulfonates (SO$_3^-$);

'Y' is either Br or I;

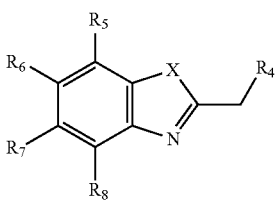

Formula II wherein,

'R$_4$' is selected from a group comprising H, alkyl, aryl, nitrile, acid and halogen, and wherein the halogen is selected from a group comprising, chloride, fluoride, bromide and iodide; and 'R$_5$', 'R$_6$', 'R$_7$' or 'R$_8$' is selected from a group comprising H, OH, alkyl, aryl, halogen, nitro, sulfonates (SO$_3^-$) and nitrile group;

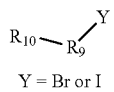

Formula III

Y = Br or I wherein,

'R$_9$' is selected from a group comprising H and —(CH$_2$)$_n$—, wherein 'n' is 1-6;

'R$_{10}$' is selected from a group comprising hydrogen, —OH, methyl, amine, terminal alkyne, alkene, alkyl acid, amine acid and sulfonates (SO$_3^-$); and, b. reacting the compound of Formula IV with compound of Formula V in presence of piperidine and alcohol.

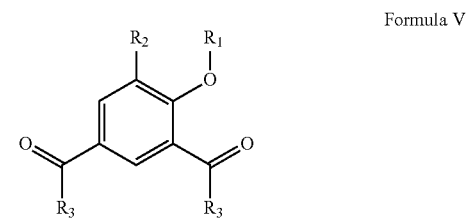

Formula V wherein,

'R$_1$' is hydrogen;

'R$_2$' is selected from a group comprising H, OH, halogen, alkyl and substituted alkyl, and wherein, the halogen is selected from a group comprising bromide, chloride and iodide; and 'R$_3$' is selected from a group comprising H, alkyl, aryl, nitrile, acid and halogen, and wherein the halogen is selected from a group comprising, chloride, fluoride, bromide and iodide;

Thus, the present disclosure relates to a method for preparing the compounds of Formula I, wherein the method comprises the act of reacting N-alkylted benzothiazole derivatives with 4-hydroxy isophthal aldehyde derivatives (Scheme 1).

Scheme 1: General scheme for the synthesis of compounds under Formula 1

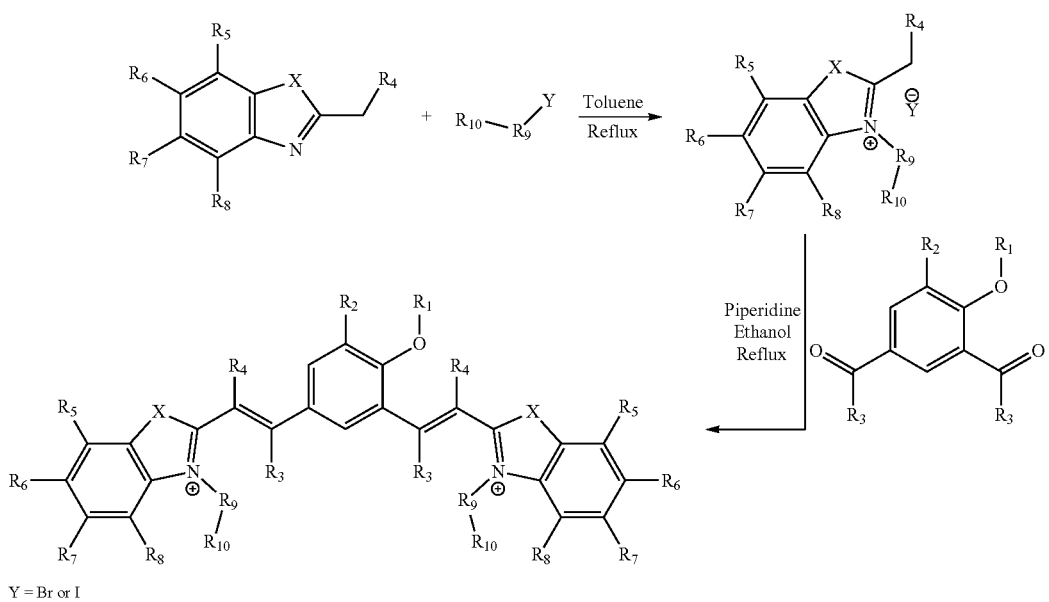

Y = Br or I

In an embodiment, the Formula I compound 4-((N,N-dimethyl,2,4-bis((E)-2-(benzo[d]thiazol-2-ylinium)vinyl)phenoxy)methyl)phenylboronic acid [QCy-BA] is prepared by
a. reacting 2-methyl benzothiazole with methyl iodide to obtain N-methyl-2-methylbenzothiazole; and
b. reacting the N-methyl-2-methylbenzothiazole with 4-(4-(4,4,5,5-tetramethyl-1,3,2-dioxaborolan-2-yl)benzyloxy)isophthalaldehydein presence of piperidine and ethanol.

The processes as described above, wherein said process is carried out at a temperature ranging from about 30° C. to 80° C., and for a time period ranging from about 2 hours to 24 hours.

The process as described above, wherein the steps a) and b) further comprise isolation, purification or a combination thereof of the corresponding product; wherein said isolation and purification is carried out by acts selected from a group comprising addition of solvent, washing with solvent, quenching, filtration, extraction, chromatography and combinations thereof.

The present disclosure also relates to pharmaceutical compositions or formulations comprising one or more compounds of Formula I, optionally along with pharmaceutically acceptable excipients. In an embodiment, the pharmaceutically acceptable excipient is selected from a group comprising adjuvant, diluent, carrier, granulating agents, binding agents, lubricating agents, disintegrating agent, sweetening agents, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient or any combination of excipients thereof. In another embodiment, the pharmaceutical composition of the present disclosure is administered to a subject through modes selected from a group comprising intravenous administration, intramuscular administration, intraperitoneal administration, hepatoportal administration, intra articular administration and pancreatic duodenal artery administration, or any combination thereof.

The present disclosure also provides for a method of protecting a fluorescent probe, particularly QCy-DT, wherein the method comprises the step of reacting QCyDT with a protecting agent. In an embodiment, the protecting agent is selected from group comprising phenyl boronate, esters, phosphates, ethers and carbonates. In another embodiment, the method provides a protected fluorescent probe QCy-BA.

The present disclosure provides a method of detecting or quantifying the presence of reactive oxygen species (ROS) in a biological sample, said method comprising the act of contacting the compound of Formula I or its salt, derivative, tautomer, isomer, polymorph, analog, solvate or intermediates thereof, or the composition comprising a compound of formula I with the sample and detecting the fluorescence indicative of the presence of ROS in the biological sample. In an embodiment of the present disclosure, ROS compound is selected from a group comprising hydrogen peroxide, tertbutyl hydroperoxide, superoxide, hydroxyl radical, tert-butoxy radical, hypochlorite and ONOO$^-$. In another embodiment of the present disclosure, the biological sample is cells, tissue, biological fluids, or combinations thereof.

The present disclosure provides a method for detecting or quantifying a ROS compound in vivo in a subject, said method comprising:

a. administering to a subject, a compound of Formula 1;
b. allowing said compound of Formula 1 to react with a ROS; and
c. detecting or quantifying the fluorescence, indicative of the presence of ROS compound in vivo.

In an embodiment of the present disclosure, detecting or quantifying further comprises detecting the location of ROS compound in said subject. In another embodiment of the present disclosure, the detection or quantifying is by technique selected from fluorescence microscopy, fluorescence spectroscopy, confocal laser scanning microscopy, total internal reflection fluorescence microscopy, Near infra-red florescence and combinations thereof. In yet another embodiment of the present disclosure, the compound of Formula I is provided as a combination probe with DNA sequences for detecting and quantifying the ROS, and wherein the DNA sequence is exogenous DNA or endogenous nuclear DNA, or a combination thereof.

In an embodiment of the present disclosure, the compound in the presence of ROS is cleaved to release a fluorescent probe quinone cyanine-dithiazole (QCy-DT), which is capable of binding to the AT-rich DNA for flouro-metric detection and quantification of the ROS The present disclosure provides for a method of diagnosing a disease condition in a subject, wherein the method comprises the step of contacting the compound of Formula I the composition comprising a compound of formula I with sample obtained from the subject. In an embodiment, the subject is a mammal or a plant, and wherein the sample from mammal is selected from group comprising blood, serum, in-vitro sample, synthetic sample, any bodily fluid and combinations thereof. In an embodiment, the sample is selected from group comprising blood, serum, in-vitro sample, synthetic sample, any bodily fluid and combinations thereof. In an embodiment, the disease is caused by the excessive presence of ROS leading to oxidative stress. In another embodiment, the ROS includes but is not limited to $H_2O_2$. In another embodiment, the disease is selected from a group comprising cancer, cardiovascular dysfunction, neurodegenerative diseases, gastroduodenal pathogenesis, inflammatory disorders, metabolic dysfunction of organs, premature aging and combinations thereof. In an embodiment of the present disclosure, the disease is diagnosed by detecting and optionally quantifying reactive oxygen species (ROS) in the sample. In an exemplary embodiment, the Formula I compound detects ROS, to diagnose the disease condition.

The present disclosure also relates to the use of Formula I compounds for detecting ROS in a sample.

The present disclosure also relates to a method of inhibiting growth of a cell, said method comprising contacting the compound of Formula I or its salt, derivative, tautomer, isomer, polymorph, analog, solvate or intermediates thereof, the composition comprising compound of formula I with the cell. In an embodiment, the cell is unicellular an eukaryotic cell selected from a group comprising cancerous cells, cells infected with microorganisms, parasite or unicellular protozoan and other cells characterized by abnormal levels of ROS, and wherein the parasite is *Plasmodium*.

The present disclosure also relates to a method of treating a disease characterized by abnormal levels of ROS in a subject, said method comprising step of administering the compound of Formula I or its salt, derivative, tautomer, isomer, polymorph, analog, solvate or its intermediates thereof, or the composition comprising compound of formula I in said subject to treat the disease.

The present disclosure also relates to the use of compound of Formula I or its salt, derivative, tautomer, isomer, polymorph, analog, solvate or intermediates thereof, or the composition of claim 8 as a probe for detecting and optionally quantifying ROS, diagnosing a disease caused by abnormal ROS levels, inhibiting growth of a cell, treating a disease characterized by abnormal levels of ROS.

The present disclosure also relates to a kit for detecting reactive oxygen species (ROS) in a sample, wherein the kit comprising the compound of formula 1 or its salt, derivative, tautomer, isomer, polymorph, analog, solvate or intermediates thereof; or a composition comprising compound of formula I, wherein the said compound is present in an amount effective to detect the presence of ROS.

The present disclosure is further described with reference to the following examples, which are only illustrative in nature and should not be construed to limit the scope of the present disclosure in any manner.

EXAMPLES

Standard Parameters:

All the chemicals, reagents, self-complementary Drew-AT, Hoechst 33258, Phosphate buffer saline (PBS), 2',7'-dichlorofluorescein (DCFDA), 5-bromo-2'-deoxyuridine (BrdU) and doxorubicin (dox) and N-acetyl-L-cysteine (NAC) are purchased from Sigma-Aldrich. All synthesized compounds are purified by column chromatography using Rankem silica gel (60-120 mesh). $^1$H and $^{13}$C NMR spectra are recorded on a Bruker AV-400 MHz spectrometer with chemical shifts reported as parts per million (ppm) (in $CDCl_3$, DMSO-$d_6$, tetramethylsilane as an internal standard) at 20° C. High resolution mass spectra (HRMS) are obtained on Agilent Technologies 6538 UHD Accurate-Mass Q-TOF LC/MS spectrometer. The UV-vis absorption and emission spectra are recorded on Agilent Technologies Cary series UV-vis-NIR absorbance and Cary Eclipse fluorescence spectrophotometers respectively. UV-vis absorption and emission spectra are measured in quartz cuvettes of 1 cm path length. HeLa cells and MRC 5 PDL 23 cells used in the biological studies are obtained from "Molecular reproduction, development and genetics lab Indian institute of science Bangalore, India".

Sample Preparation for UV-Vis and Fluorescence Measurements

All biophysical studies (UV-vis and fluorescence) are carried out at the concentration 0-5 μM of probe, volume=500 μL, temperature=25° C. and time of incubation=2 min. Stock solution of probe QCy-BA is prepared in milli molar concentration in milli Q-water (MQ-water) and stored at −10° C. DNA stock solutions are prepared by dissolving oligos in double distilled water in the order of $10^{-4}$ M. Double stranded DNA samples are prepared in PBS (10 mM, pH=7.4) buffer solution and subjected to annealing by heating up to about 85° C. for 15 minutes and subsequently cooled to room temperature for 7 h and stored in refrigerator for about 4 hours.

HeLa Cells Maintenance:

Human cervix carcinoma cell line (HeLa) is cultured in DMEM (Dulbecco's Modified Eagal's Medium) with 10% FBS (Fetal Bovine Serum). The antibiotics pencilin and streptomycin (1%) is mixed with 10% FBS medium. The cells are incubated at 37° C. temperature and 5% $CO_2$ humidified chamber. All cell culture work is carried out under laminar flow hood and auspicious conditions.

Cytotoxicity Studies on HeLa Cells (MTT Assay):

MTT [(3-(4,5-dimethylthiozol-2yl)-2,5-diphenyltetrazolium bromide] assay is carried out with probe QCy-BA on HeLa cells to determine the cytotoxicity effect. In a tissue cultured 96-well plate, 10,000 cells per well are plated and incubated for 24 h, for cells to attach. After completion of 24 h incubation, the attached and healthy cells are treated with various concentrations (25 μM, 12.5 μM, 6.25 μM, 3.125 μM and 0 μM) of probe QCy-BA and further incubated for 24 h. All the treatments are carried out in triplicates. The required concentrations of QCy-BA are made from stock solution in 0.2% DMEM. Stock solution of probe QCy-BA (1 mg/mL) is made in water. Four hours before stipulated time of experiment, MTT-solution (5 mg/mL of 20 μL) is added in each well and incubated to form formazan crystals. The culture medium is completely removed by 1 mL pipette and 200 μL of DMSO is added to dissolve formazan crystals. The purple colored formazan is estimated by determining absorbance at 590 nm with the help of spectrophotometer (Bio-RAD model 1680, Microplate reader). The results are shown in bar graphs (concentration of QCy-BA vs % cell viability).

Exogenous and Endogenous Detection of $H_2O_2$ in HeLa Cells by QCy-BA:

In each well, $3 \times 10^6$ cells are plated in 12-well tissue culture plates and incubated for 24 hours. These cells are serum deprived for 1 h. In addition, the serum deprived cells of 6-well are treated with N-acetyl-L-cysteine (NAC) (8 mM) solution and incubated for 1 hour and cells are treated with probe QCy-BA (5 μM) and incubated for 30 minutes. After 30 minutes incubation, the cells are washed with DPBS (Dulbecco's Phosphate buffer saline) to remove the excesses of QCy-BA. These cells are harvested after trypsinization. Exogenously, $H_2O_2$ (100 μM) is added to QCy-BA and NAC+QCy-BA treated cells and incubated for 15 min. These samples are subjected to FACS analysis.

Epidermal Growth Factor (EGF) Produced $H_2O_2$ Detection by QCy-BA in HeLa Cells:

To determine the EGF produced ROS in cells by QCy-BA. In a 12-well plate, $3 \times 10^6$ HeLa cells are plated in each well and incubated for 24 hour. These cells are serum deprived for 1 h. Cells are incubated with EGF (500 ng/mL) for 40 minutes and further treated with NAC (8 mM) for 1 hour. Then cells are treated with QCy-BA (5 μM) for 30 minutes. After 30 minutes incubation of cells with QCy-BA, cells are washed with DPBS (Dulbecco's Phosphate Buffer Saline) to remove the excesses of QCy-BA. These cells are harvested after trypsinization. The samples are subjected to FACS.

Immunofluorescence Studies with QCy-BA for Detection of $H_2O_2$ in HeLa Cells:

An Immunofluorescence studies are carried out on HeLa cells to validate exogenous and endogenous detection of $H_2O_2$ by QCy-BA. The HeLa cells (10,000 cells) are grown on cover slips. These cells are treated with 5 μM concentration of QCy-BA for 30 minutes. The cells are washed with DPBS for several times to remove the excesses of QCy-BA. The cells are treated with $H_2O_2$ (100 μM) for 30 minutes. These samples are subjected to confocal microscopy for immunefluorescence images.

Detection Limit of $H_2O_2$ in Presence of QCy-BA:

Concentration dependent studies are performed using microplate reader. In the well-plates, first QCy-BA (5 μM) in buffer solution is taken, then increasing concentration of $H_2O_2$ from 0 to 100 μM is added. Upon excitation at 400 nm, the emission at 550 nm as function time after addition of $H_2O_2$ is collected. The fluorescence intensity at 550 nm is plotted as a function of concentration of hydrogen peroxide and each experiment is done in triplicates.

Detection of ROS Using Fluorescence Plate Reader:

The cells are incubated with QCy-BA (5 μM) for 30 minutes in dark, washed with PBS and analysed to detect QCy-BA dye fluorescence using Infinite M1000 Pro, Tecan, Austria). Wavelengths used for excitation and emission for QCy-BA dye is 400 nm/650 nm. In all ROS measurement assays are done using plate reader and after fluorescence measurements, cells are washed, trypsinized and counted to estimate fluorescence per cell recordings.

Live Cell Imaging of MRC5 Cells:

MRC5 PDL 23 cells are seeded overnight and treated with Hydrogen Peroxide to do live cell imaging after addition of QCy-BA (5 μM) for 30 minutes. Images are acquired using Olympus IX 83 inverted epifluorescence microscope using a 20× objective.

Absorption and Emission Spectra:

The UV-vis absorption spectra are recorded on a Perkin Elmer Model Lambda 900 spectrophotometer. Emission spectra are recorded on Perkin Elmer Model LS 55 spectrophotometer. Temperature dependent absorption measurements (UV-Vis melting studies) are carried out on Cary 5000 UV-vis-NIR spectrophotometer equipped with Cary temperature controller in the range of 10° C. to 90° C. with ramp rate of 1° C./min.

Example 1: Preparation of QCy-BA

Synthesis of QCy-BA is achieved by treating 4-(hydroxymethyl)phenyl boronic acid with a pinacol in the presence of magnesium sulfate in acetonitrile to obtain 4-(hydroxymethyl)phenylboronic ester (1). The phenylboronic ester 1 is treated with NaI and trimethylsilyl chloride in acetonitrile at 4° C. to give 4-(iodomethyl)phenylboronic ester (2). The 4-(iodomethyl)phenyl boronic ester (2) is coupled to 4-hydroxy isophthaldehyde using potassium carbonate as a base in dimethylformamide (DMF) at room temperature to obtain phenyl boronic ester dialdehyde (3) in good yield. Finally, the dialdehyde (3) is coupled with N-methylated benzothiazolein the presence of piperidine to yield the probe QCy-BA. All the intermediates and probe QCy-BA are characterized by NMR and high-resolution mass spectroscopy (HRMS).

The overall synthesis of QCy-BA has been described below in a schematic fashion. Also, the preparation of the intermediates has been described below individually which leads to the preparation of QCy-BA.

Scheme 2: Synthesis of QCy-BA

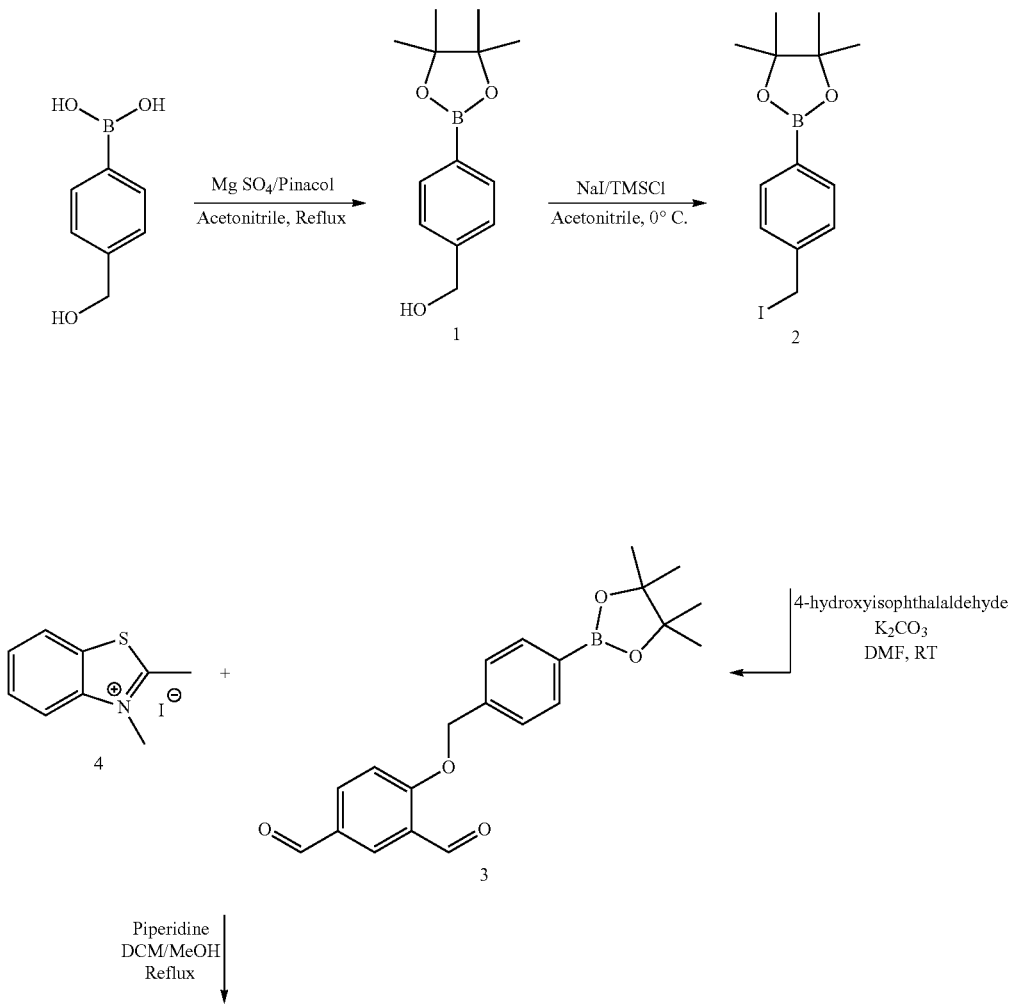

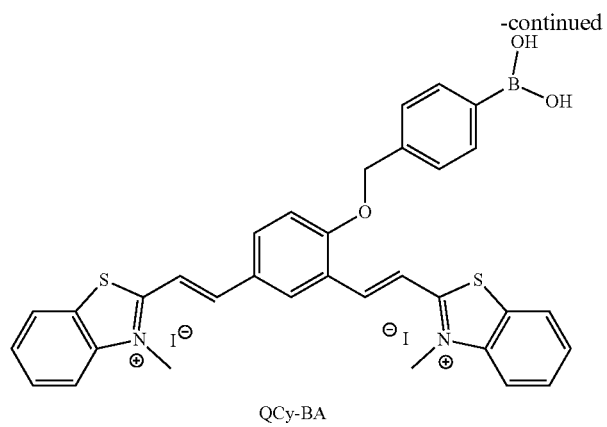

QCy-BA a) Synthesis of Compound 1 (4-(4,4,5,5-tetramethyl-1,3,2-dioxaborolan-2-yl)phenyl) methanol b) Synthesis of compound 2 (2-(4-(iodomethyl)phenyl)-4,4,5,5-tetramethyl-1,3,2-dioxaborolane)

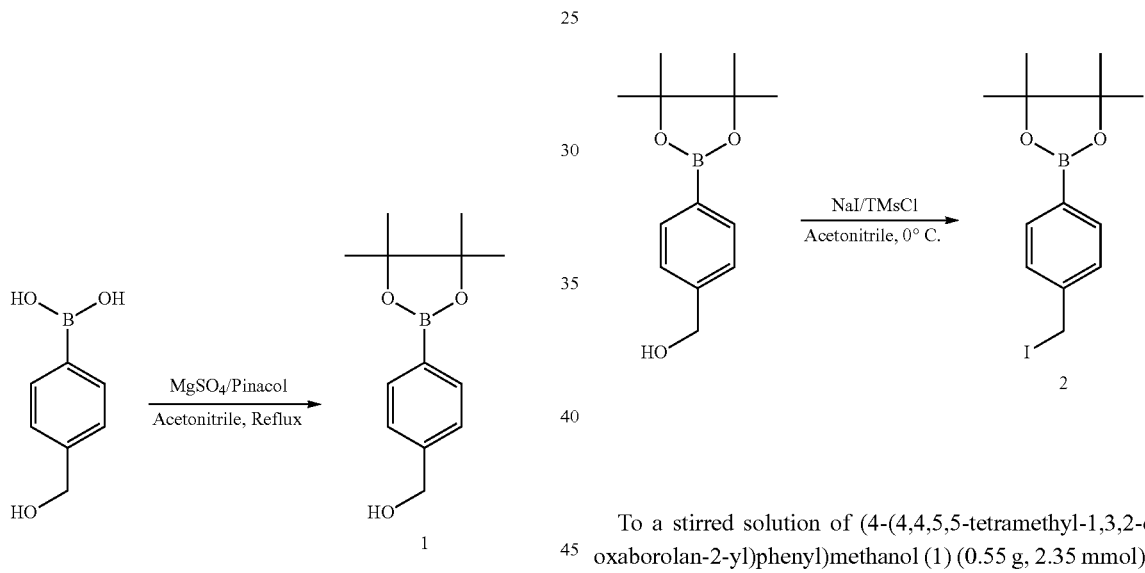

To a stirred solution of 4-(hydroxymethyl) phenylboronic acid (0.4 g, 2.63 mmol) in acetonitrile (15 mL), MgSO$_4$ (3 g) and pinacol (0.37 g, 3.15 mmol) are added. The reaction mixture is heated up to about 80° C. and allowed to reflux for about 24 hours. After completion of the reaction, solvent is evaporated under vacuum. The crude mixture is dissolved in dichloromethane and filtered. The obtained product (4-(4,4,5,5-tetramethyl-1,3,2-dioxaborolan-2-yl)phenyl) methanol (i.e. compound 1) is used for further reaction without purification.

To a stirred solution of (4-(4,4,5,5-tetramethyl-1,3,2-dioxaborolan-2-yl)phenyl)methanol (1) (0.55 g, 2.35 mmol) in acetonitrile (20 mL), sodium iodide (1.1 g, 7.05 mmol) and Trimethylsilyl chloride (0.65 mL, 7.05 mmol) are added at about 0° C. The reaction mixture is allowed to stir at room temperature for about 1 hour. After completion of the reaction, solvent is evaporated under vacuum. The crude product is dissolved in saturated solution of Na$_2$S$_2$O$_3$ to quench the unreacted iodide and the product is extracted with dichloromethane. The crude product is purified by column chromatography on silica gel using ethyl acetate-hexane (5:95) as an eluent to give product 2-(4-(iodomethyl)phenyl)-4,4,5,5-tetramethyl-1,3,2-dioxaborolane (2) in excellent yield (90%).

$^1$H NMR (400 MHz, CDCl$_3$) $\delta_{ppm}$ 7.73 (d, J=8 Hz, 2H), 7.37 (d, J=8 Hz, 2H), 4.45 (s, 2H), 1.34 (s, 12H) (FIG. 18).

$^{13}$C NMR (100 MHz, CDCl$_3$) $\delta_{ppm}$ 142.3, 135.3, 128.0, 24.9, 5.4 (FIG. 19).

c) Synthesis of compound 3 (4-(4-(4,4,5,5-tetramethyl-1,3,2-dioxaborolan-2-yl)benzyloxy)isophthalaldehyde

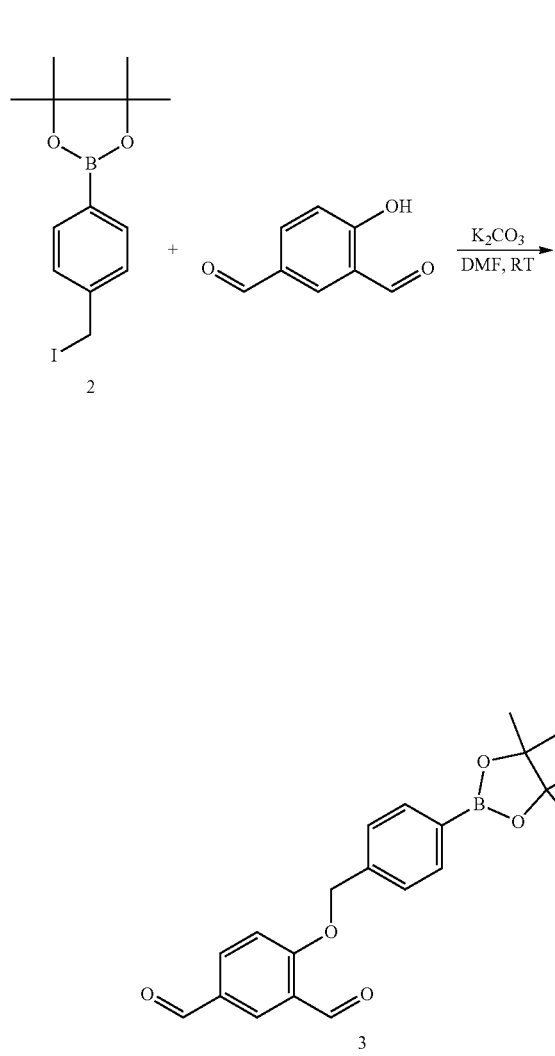

To a stirred solution of 4-hydroxyisipthaladehyde (0.11 g, 0.73 mmol) in Dimethylformamide (DMF) (5 mL), K$_2$CO$_3$ (0.3 g, 2.17 mmol) is added and allowed to stir for about 20 minutes. After about 20 minutes, 2-(4-(iodomethyl)phenyl)-4,4,5,5-tetramethyl-1,3,2-dioxaborolane (2) (0.3 g, 0.87 mmol) is added and stirred overnight at room temperature (RT). The completion of reaction is monitored by TLC. After completion of the reaction, solvent is evaporated and product is extracted with diethylether (3×100 mL). The crude product is purified by column chromatography on silica gel using ethyl acetatehexane (20:80) as an eluent to obtain compound 3 in good yield (60%).

$^1$H NMR (400 MHz, CDCl$_3$) $\delta_{ppm}$ 10.56 (s, 1H), 9.95 (s, 1H), 8.35 (d, J=2.4 Hz, 1H), 8.08 (dd, J=2 Hz, 8.8 Hz, 1H), 7.86 (d, J=8 Hz, 2H), 7.44 (d, J=8 Hz, 2H), 7.17 (d, J=8 Hz, 1H), 5.32 (s, 2H), 1.35 (s, 12H) (FIG. 20).

$^{13}$C NMR (100 MHz, CDCl$_3$) $\delta_{ppm}$ 190.1, 188.5, 164.9, 137.9, 135.5, 135.3, 131.9, 129.9, 126.5, 125.2, 113.7, 84.0, 71.0, 24.9 (FIG. 21).

d) Synthesis of QCy-BA

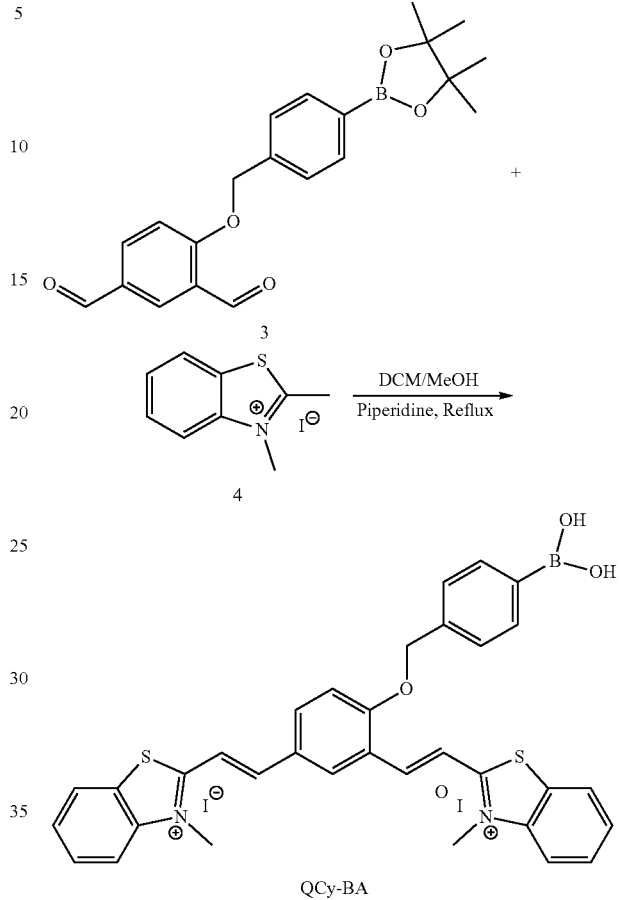

To a stirred solution of N-methylated, 2-methyl benzothiazolinium (compound 4) (80 mg, 0.27 mmol) in methanol (10 mL) and dichloromethane (5 mL), piperidine (8 μL) is added and allowed to stir for about 10 minutes. After about 10 minutes, 4-(4-(4,4,5,5-tetramethyl-1,3,2-dioxaborolan-2-yl)benzyloxy)isophthalaldehyde (compound 3) (45 mg, 0.12 mmol) in dichloromethane (DCM) (2 mL) is added and heated up to about 50° C. for about 3 hours. After the completion of reaction, the solvent is evaporated. The crude brown color solid is washed with diethylether (50 mL) to remove the unreacted starting materials. The brown solid is dissolved in acetonitrile/water mixture and purified by reverse phase HPLC using 0.1% trifluoroacetic acid (TFA) in water/acetonitrile (50-100%) as a mobile phase to obtained boronic acid conjugate (QCy-BA) in moderate yield 30%.

$^1$H-NMR (400 MHz, DMSO-d$_6$) $\delta_{ppm}$ 8.69 (d, J=2 Hz, 1H), 8.44 (ddd, J=2.8 Hz, J=4.0 Hz, J=7.6 Hz, 2H), 8.34-8.25 (m, 4H), 8.21 (d, J=4.2 Hz, 1H), 8.16 (d, J=12.4 Hz, 1H), 8.10 (d, J=8.2 Hz, 1H), 7.92-7.88 (m, 4H), 7.81 (td, J=0.8 Hz, J=7.6 Hz, 2H), 7.56 (dd, J=4 Hz, J=8.4 Hz, 3H), 5.48 (s, 2H), 4.39 (s, 3H), 4.25 (s, 3H) (FIG. 22).

$^{13}$C-NMR (100 MHz, DMSO-d$_6$) $\delta_{ppm}$ 171.9, 171.8, 160.6, 158.3, 158.0, 147.0, 142.1, 142.0, 141.6, 137.5, 135.0, 134.5, 132.3, 129.5, 129.4, 128.6, 128.4, 127.9, 127.8, 127.3, 127.0, 124.3, 124.2, 123.1, 118.1, 117.0, 116.9, 115.6, 115.1, 114.4, 113.0, 71.0, 36.4, 36.2 (FIG. 23).

HRMS (ESI-MS): found 288.0875, calcd m/z=288.0851 for $C_{33}H_{29}BN_2O_3S_2$ $[M-2I]^{2+}$ (FIG. 24).

Example 2: NMR-Analysis of $H_2O_2$ Triggered Release of DNA Minor Groove Binder In a preliminary study, time-dependent NMR spectroscopy analysis of QCy-BA is carried out in the presence of $H_2O_2$ to assess the stimuli-responsive slicing of phenyl boronic acid functionality (FIG. 1(a)). The $^1H$ NMR spectrum of QCy-BA (2 mM) alone in $D_2O$ (0.5 mL) showed a single peak at 5.05 ppm corresponding to the O—$CH_2$(C—$H_a$)-bearing phenyl boronic acid group and peaks at 8.2-7.2 ppm corresponding to aromatic protons of the parent QCy-DT.

The chemical shifts of O—$CH_2$, aromatic region of QCy-BA and appearance of possible new peaks for p-quinonemethide (sliced byproduct corresponding to phenyl boronic acid functionality) upon sequential addition of $H_2O_2$ is monitored. After about 1 hour of $H_2O_2$ (10 mM, 5 μL from the stock $H_2O_2$ of 1M) addition, the peak intensity at 5.05 ppm, i.e., C—$H_a$(O—$CH_2$) gradually decreased and new peaks appeared at 5.20 ppm and 6.5-7.0 ppm regions, suggesting the coexistence of both phenyl boronic acid protected and deprotected forms of QCy-BA. The peaks at 5.20 ppm and aromatic region 6.5-7.0 ppm correspond to the newly-formed exocyclic C—$H_b$ protons of p-quinone-methide and QCy-DT moieties, respectively. After about 2 hours, a single peak at 5.20 ppm and prominent new peaks at 6.5-7.0 ppm are observed, indicating the complete conversion of QCy-BA to QCy-DT and p-quinonemethide (FIG. 1(b)). This study confirmed the $H_2O_2$ stimulus-triggered slicing of phenyl boronic acid functionality of QCy-BA to release QCy-DT, a DNA minor groove binding probe. It is observed that the color of the solution changes from yellow to brown after the addition of $H_2O_2$ to QCy-BA, a naked eye detection of the formation of p-quinone-methide and QCy-DT (FIG. 1(c)).

Example 3: Photo-Physical Properties of QCy-BA in Presence of $H_2O_2$

Next, the photophysical properties of QCy-BA in the absence and presence of $H_2O_2$ are studied using UV-vis absorption and emission studies in PBS-buffer solution (10 mM, pH=7.4) under ambient conditions.

UV-vis absorption spectrum of QCy-BA (5 μM) showed broad absorbance in the 300-500 nm region with absorption maximum ($\lambda_{max}$) at 400 nm. Upon excitation at 400 nm, emission spectrum of QCy-BA (5 μM) showed weak fluorescence with emission maximum ($E_{max}$) at 565 nm (FIG. 6(b)). As expected, QCy-BA did not emit in the NIR region due to phenyl boronic acid protection of backbone-phenolic hydroxyl moiety.

Figure 1:
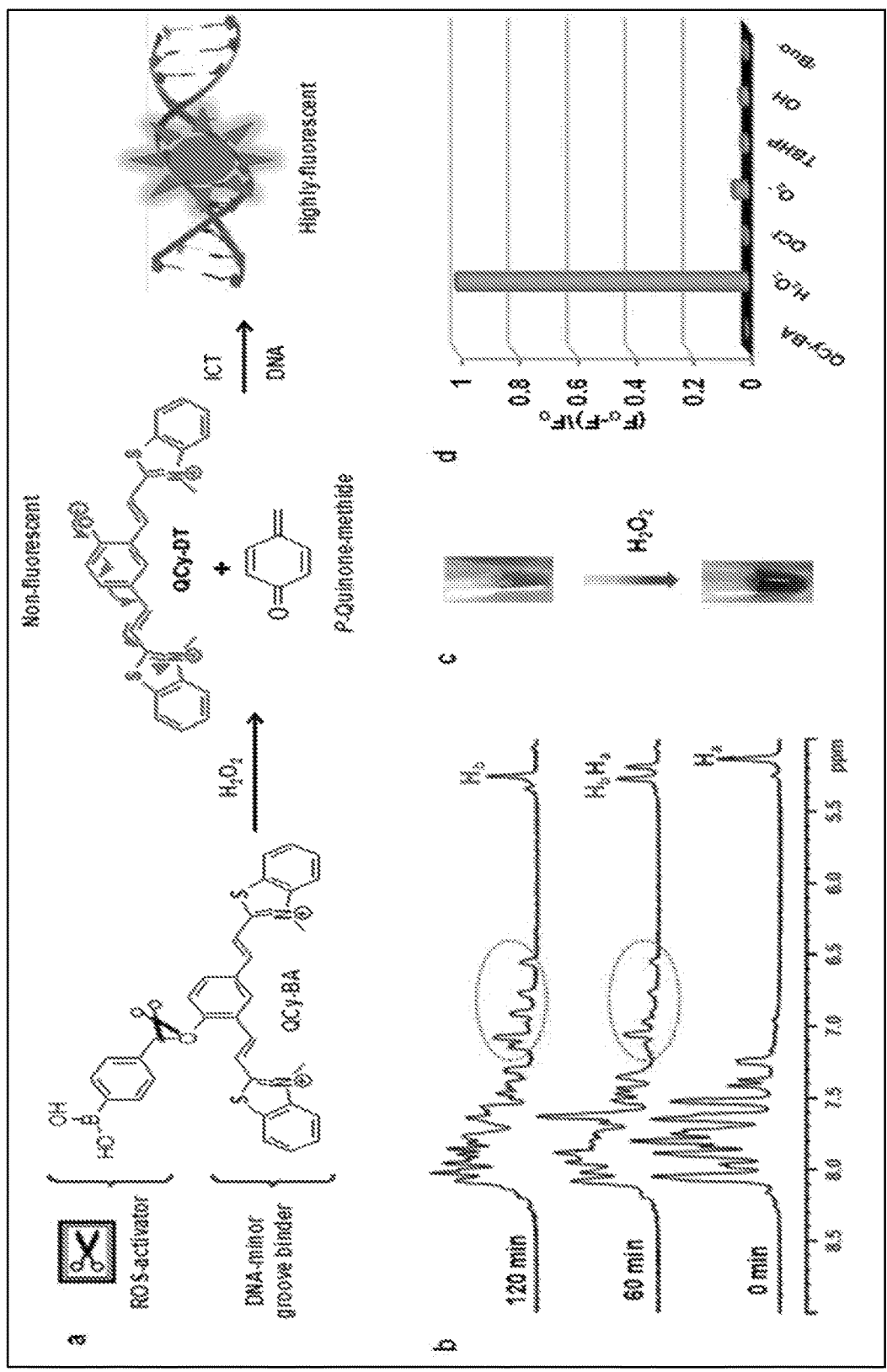
FIG. 1 depicts H$_2$O$_2$ triggered release of NIR-fluorescence minor groove binder.

Interestingly, absorption spectrum of QCy-BA (5 μM) showed a gradual decrease in absorption maxima at 400 nm in presence of $H_2O_2$ (1 mM); this is accompanied by the appearance of a new absorption band at 465 nm with a shoulder at 530 nm and an isosbestic point at 442 nm (FIG. 6(a)). The new absorption bands at 465 nm and 530 nm revealed the transformation of QCy-BA to the phenolate form of QCy-DT. In agreement with the NMR study (FIG. 1(b)), UV-vis absorption data confirmed the generation of QCy-DT through $H_2O_2$-assisted oxidation of boronic acid in QCy-BA followed by the hydrolysis and 1,6-elimination of p-quinone-methide group. Evidently, UV-vis absorption spectral characteristics clearly support the observed change in solution color from yellow to brown, as a result of the newly formed QCy-DT ($\lambda_{max}$ at 465 and 530 nm) from QCy-BA ($\lambda_{max}$=400 nm) as seen in FIG. 1 (c).

The emission spectra of QCy-BA (5 μM) in the presence of $H_2O_2$ (1 mM) displayed gradual decrease in fluorescence intensity at 565 nm and a weak basal level fluorescence band centered around 680 nm with a large Stokes shift ($\Delta\lambda_{max}$=~280 nm) upon excitation at 400 nm (FIG. 6(b)). Therefore, $H_2O_2$.triggered slicing of phenyl boronic acid functionality of QCy-BA is a highly useful transformation for the generation of stimuli-responsive switch-on DNA binding fluorescence probe QCy-DT owing to its large Stokes shift and non-fluorescence in the unbound state.

Example 4: Concentration-Dependent Fluorescence Study of QCy-BA

Further, concentration-dependent fluorescence study on slicing of the phenyl boronic acid functionality of QCy-BA (5 μM) in response to sequential addition of $H_2O_2$ (5 to 100 μM) is performed. The fluorescence intensity of QCy-BA at 565 nm is decreased in response to added $H_2O_2$ in the concentration range of 5 to 50 μM and subsequently reached saturation at 100 μM. A linear relationship ($R^2$=0.9877) is observed with increasing concentration of $H_2O_2$ in the concentration range of 5-50 JAM. Based on 3a/slope the limit of detection (LOD) of $H_2O_2$, using the decrease in fluorescence of QCy-BA at 565 nm, is found to be 5.3 μM (FIG. 7). $H_2O_2$ is one of the many ROS present in the biological system and it is necessary to test the probe QCy-BA against all of them to assess the selectivity and specificity. Therefore, the response of QCy-BA towards $H_2O_2$ (100 μM) in the presence of other ROS (100 μM) is examined, including tertbutyl hydroperoxide (TBHP), superoxide ($O_2^-$), hydroxyl radical (HO.), tert-butoxy radical ($^tBuO.$) and hypochlorite ($OCl^-$). Remarkably, $H_2O_2$ efficiently decreased the fluorescence emission at 565 nm owing to selective slicing of phenyl boronic acid functionality of the QCy-BA (5 μM). On the other hand, very minimal or no effect on the probe response in the presence of superoxide ($O_2^-$), hydroxyl radical (HO.), tert-butoxy radical ($^tBuO.$) and hypochlorite ($OCl^-$) (FIG. 1(d)) is observed. These results are in agreement with the selective 1,6-elimination of phenyl boronic acid functionality of QCy-BA in the presence of $H_2O_2$ to liberate p-quinone-methide moiety and QCy-DT.

Example 5: Photo-Physical Properties of Combination Probe QCy-BA ⊂ Drew-AT in Presence of $H_2O_2$ To further validate the $H_2O_2$-stimulated conversion of QCy-BA to QCy-DT, a DNA minor groove binder, the transformation is monitored using UV-vis absorption and emission studies in the presence of an AT-rich DNA strand (Drew-AT: 5'-GCGCAAATTTGCGC-3'). QCy-DT binds AT-rich DNA minor groove with high sequence-specificity (5'-A<u>AATT</u>T-3'), which reflects in the strong NIR-fluorescence. Thus, Drew-AT is chosen, a self-complementary 14-base pair (bp) sequence containing central 5'-A<u>AATT</u>T-3' sequence for fluorescence reporting of QCy-DT released in response to $H_2O_2$ stimulus, by means of strong emission in the NIR region. The absorption spectrum of QCy-BA (2 μM) in the presence of Drew-AT (2 μM) duplex showed an increase in absorption maxima at 416 nm with bathochromic shift ($\Delta\lambda_{max}$=16 nm) (FIG. 8 (a)). On the other hand, the fluorescence spectrum of QCy-BA (2 μM) in the presence of Drew-AT showed emission maxima at 500 nm with hypsochromic shift ($\Delta\lambda_{max}$=~50 nm) (FIG. 8(b)). These changes in absorption and emission spectra are attributed to weak interactions between QCy-BA and Drew-AT duplex through electrostatic and hydrophobic interactions.

Next, absorption and emission spectra of QCy-BA are recorded in the presence of Drew-AT duplex and $H_2O_2$ (100 μM). The absorption spectrum showed a gradual decrease in absorption at 416 nm with corresponding increase in the absorption at 564 nm with an isosbestic point at 456 nm, which is in agreement with the absorption characteristics observed for QCy-DT/Drew-ATcomplex (FIG. 2(a)). Similarly, the emission spectrum of QCy-BA (excitation at $\lambda_{max}$=400 nm) in the presence of Drew-AT duplex and $H_2O_2$ showed fluorescence decrease at 500 nm and corresponding increase at 650 nm (FIG. 2(b)). This remarkable ratiometric emission at 500 nm and 650 nm ($\Delta\lambda_{max}$=~250 nm) is a desirable property of a fluorescence probe to increasing signal-to-noise ratio; measurement at low wavelengths minimizes the error arising from various environmental factors. Further, upon excitation at 564 nm ($\lambda_{max}$ of QCy-DT bound to Drew-ATduplex), strong fluorescence enhancement at 650 nm is observed (FIG. 2(c)). These results reiterated that the $H_2O_2$-triggered conversion of QCy-BA to a DNA minor groove binder QCy-DT is a promising ratiometric fluorescence platform for $H_2O_2$ detection in the presence of exogenous DNA (Drew-AT).

Time-Dependent Fluorescence Study to Analyse Release Kinetics of QCy-BA to QCy-DT in Response to $H_2O_2$ The time-dependent fluorescence study is carried out to evaluate the release kinetics of QCy-BA (2 μM) to QCy-DT in response to $H_2O_2$ (100 μM) stimulus, in presence of Drew-AT duplex. The change in fluorescence intensities at 500 nm and 650 nm corresponding to emission maxima ($E_{max}$) of QCy-BA and QCy-DT in presence of Drew-AT is monitored. Upon excitation at 400 nm, fluorescence intensity of QCy-BA gradually decreased at 500 nm while that of QCy-DT increased at 650 nm (FIG. 2(d)).

Similarly, the fluorescence spectra recorded upon excitation at 564 nm showed an exponential increase in emission intensity at 650 nm as a function of time and reached saturation ≥4 hours (FIG. 9). The calculation of kinetics parameter using pseudo-first-order conditions for conversion of QCy-BA (2 μM) to QCy-DT in the presence of $H_2O_2$ (1 mM) and Drew-AT (2 μM) gave the rate constant of $k_{obs}$=1.0×10$^{-3}$ s$^{-1}$ (FIG. 10).

Overall, photo-physical (absorption and emission) studies demonstrated that $H_2O_2$ triggers the slicing of phenyl boronic acid functionality of QCy-BA to generate QCy-DT, a DNA minor binding probe that shows switch-on NIR-fluorescence in the presence of Drew-AT duplex (FIG. 2e).

Example 6: Probing of In Situ Generated $H_2O_2$ Using Combination Probe QCy-BA ⊂ Drew-AT In biological systems, enzymes such as, oxidases generate $H_2O_2$ by the oxidation of numerous biochemicals. Glucose oxidase (GOx) is one of the most important enzymes known to selectively catalyze the oxidation of glucose to gluconic acid in the presence of oxygen to generate $H_2O_2$. In this context, in situ generation of $H_2O_2$ by the oxidation of glucose in the presence of GOx using the combination probe QCy-BA ⊂ Drew-AT (FIG. 3 (a)) is investigated. To monitor the in situ generation of $H_2O_2$, glucose is added to PBS buffer (10 mM, pH=7.4) containing GOx (4 U/mL) and QCy-BA ⊂ Drew-AT (2 μM). The reaction mixture showed a gradual decrease in fluorescence at 500 nm ($\lambda_{max}$=400 nm) and corresponding increase in fluorescence intensity at 650 nm (FIG. 1 (a)).

Similarly, upon excitation at 564 nm, the fluorescence spectra showed strong enhancement in fluorescence emission at 650 nm, which may be attributed to the release and binding of QCy-DT to Drew-AT (FIG. 3(b)). Next, the reaction kinetics of in situ generation of $H_2O_2$ through the oxidation of glucose by GOx is investigated using the combination probe, upon excitation at 564 nm. The plot of fluorescence intensity at 650 nm as a function of time, after addition of glucose, is shown in FIG. 3(c). Upon addition of glucose (1 mM) in the presence of GOx, QCy-BA ⊂ Drew-AT showed gradual increase in fluorescence intensity at 650 nm and reached saturation at 1 hour. However, in the absence of glucose, GOx and QCy-BA ⊂ Drew-AT did not show such increase in fluorescence intensity. Further, the fluorescence is monitored by adding increasing concentration of glucose (0 to 1 mM) to the mixture of GOx and QCy-BA ⊂ Drew-AT. The fluorescence emission at 650 nm increases and showed a linear relationship in the concentration range of 0 to 0.2 mM (FIG. 3(d), and FIG. 11 (b)). Based on 3σ/slope, the LOD of $H_2O_2$ is found to be 6.11 μM (from the concentration of glucose) and is in good agreement with LOD of $H_2O_2$ (5.33 μM) using the combination probe (FIG. 12).

From the pseudo-first-order calculations, combination probe QCy-BA ⊂ Drew-AT (2 μM) showed the rate constant of $k_{obs}$=6.87×10$^{-4}$ s$^{-1}$ in the presence of Gox (4 U/mL) and glucose (1 mM) (FIG. 13). Overall, Gox assay demonstrated the in situ monitoring of $H_2O_2$ generated from the oxidation of glucose.

Example 7: Study of Effect of Catalase on the Combination Probe QCy-BA ⊂ Drew-AT Effect of enzyme that spontaneously decomposes $H_2O_2$, resulting in the conversion of QCy-BA to QCy-DT by the action $H_2O_2$ is studied. Catalase is one of the most efficient enzymes that convert $H_2O_2$ to water and oxygen to protect cells from oxidative damage and ROS. Catalase exhibits highest turnover number for $H_2O_2$ and capable of decomposing almost 10$^6$ molecules per second to water and oxygen. Interestingly, the fluorescence emission is not observed at 650 nm upon addition of $H_2O_2$ (1 mM) to a solution of QCy-BA ⊂ Drew-AT (2 μM) containing catalase (4 U/mL). The seized fluorescence emission at 650 nm can be attributed to the prevention of QCy-BA to QCy-DT conversion, as the added $H_2O_2$ was used as a substrate by the catalase (FIG. 14). These results validate that the combination probe QCy-BA ⊂ Drew-AT is a promising molecular tool for monitoring the in situ turnover of $H_2O_2$ involving oxidase and catalases.

Example 8: Fluorescence Imaging and Cytotoxicity Studies of QCy-BA in Presence of $H_2O_2$ Remarkable selectivity of QCy-BA towards $H_2O_2$ and its detection through DNA-assisted switch-on NIR fluorescence led to evaluation of the uptake and application of the probe to detect $H_2O_2$ in cells. For this purpose, confocal fluorescence imaging of HeLa cells treated with $H_2O_2$ (exogenous) is carried out. First, the HeLa cells are incubated with QCy-BA (5 μM) for about 30 minutes and imaged under a confocal microscope. Fluorescence images of HeLa cells showed weak fluorescence under the blue channel and no emission in the red channel (FIGS. 4(a) and 4(b)). HeLa cells containing QCy-BA are then treated with $H_2O_2$ (100

μM) for about 15 minutes, after which the cells are again scanned under a confocal microscope. Confocal images of these cells showed strong fluorescence in the red channel with maximum localization in the cell nucleus (FIGS. 4(c) and 4(d). Interestingly, cells also showed the pattern of black nucleoli, a characteristic feature of specific DNA minor groove binders over single-strand DNA and RNAs.

In order to check the cytotoxicity of probe QCy-BA cell viability assay is performed in HeLa cells. Upon incubation with QCy-BA, more than 80% of the cells are viable even at 25 μM concentration after about 24 hours (FIG. 15).

In general, above results confirm the permeability and non-toxicity (at standard working concentration and time of about 5 μM and 24 hours, respectively) of QCy-BA, and detection of exogenously added $H_2O_2$ in HeLa cells through selective fluorescence staining of the cell nucleus. Therefore, the probe of the present disclosure is permeable, non-toxin and is capable of detecting $H_2O_2$ in cells.

Example 9: Monitoring of In Situ Generated $H_2O_2$ Levels by EGF/Nox Pathways and Post-Genotoxic Stress in Live Cells NMR, photophysical study. GOx-assay and confocal fluorescence imaging of HeLa cells showed the detection of exogenously added $H_2O_2$ using QCy-BA. Next. QCy-BA for probing cellular (physiologically generated) $H_2O_2$ levels in live cells is employed. HeLa cells are incubated with QCy-BA (about 5 μM) for about 30 minutes in the absence and presence of N-acetyl-L-cysteine (NAC), a well-known $H_2O_2$ scavenger. In the absence of NAC, flow cytometry analysis of cells treated with the probe (about 5 μM) showed an increase in mean fluorescence intensity of PerCP as compared to control cells (FIG. 16). Upon addition of NAC (8 mM), fluorescence intensity of PerCP decreased significantly (FIG. 4(e)). In a control experiment, flow cytometry analysis of live HeLa cells treated with QCy-BA and $H_2O_2$ (100 μM) for about 30 minutes at 37° C. showed an increase in the mean fluorescence intensity of PerCP (FIG. 4(e)). Thus, probe QCy-BA is also capable of detecting the cellular $H_2O_2$ levels in live cells.

Further, the study is extended to visualize the in situ $H_2O_2$ generation by a known signaling pathway in live cells. Well-known epidermal growth factor (EGF) binding to epidermal growth factor receptor (EGFR) signaling pathway is selected, which stimulates the production of $H_2O_2$ in cells by activating the NOX/PI3K pathways. In this experiment, live HeLa cells are incubated with the epidermal growth factor (EGF) (500 ng/mL) for about 40 minutes under physiological conditions (37° C., pH=7.4). EGF-treated live HeLa cells are incubated with QCy-BA (5 μM) for 30 minutes and flow cytometry analysis of these cells showed strong fluorescence intensity in the PerCP region (FIG. 4(f)). On the other hand, the control experiment performed on live HeLa cells without EGF stimulation showed modest fluorescence due to the presence of cellular $H_2O_2$ level. In contrast, NAC-treated cells showed a decrease in the fluorescence even in the presence of EGF (FIG. 4(f)). These results provided concrete evidence that QCy-BA is a versatile and practically viable molecular probe for monitoring concentration levels of $H_2O_2$ in live cells.

In order to detect the in situ generated $H_2O_2$ in other physiological conditions, fluorescent plate reader-based studies for cellular senescence in primary and cancer cells are performed using probe QCy-BA. First, the confocal fluorescence imaging of primary cells using probe QCy-BA in the presence of $H_2O_2$ is performed. Live cell imaging of MRC5 cells showed NIR fluorescence in the nucleus compared with control cells incubated with probe QCy-BA (51M) for about 30 minutes after treating with $H_2O_2$ (100 μM) (FIG. 5 (a-d)). It is well-established that genotoxic stress causes accumulation of DNA damage in cells that can trigger the generation of $H_2O_2$ inside the cells. It has also been shown that DNA damage induced cell cycle arrest, termed as cellular senescence where ROS played an integral role.

To measure ROS generated concomitant to the dose of the DNA damage, HeLa cells are treated with increasing doses (0 to 200 μM) of 5-bromo-2'-deoxyuridine (BrdU). BrdU is a thymidine analog, which gets directly incorporated into DNA and triggers DNA damage response. From previous studies in the art it is known that 48 hours of treatment with BrdU (100 μM) or another DNA damaging agent, doxorubicin at a concentration of 0.1 μM can lead to the induction of cellular senescence. After about 48 hours of treatment with BrdU (100 μM), HeLa cells showed a 3-fold increase in fluorescence of 2',7'-dichlorofluorescin diacetate (DCFDA) compared to control cells; DCFDA is a known ROS probe for live cells (FIG. 17). Interestingly, probe QCy-BA showed almost 10-fold increase in fluorescence compared to control cells unlike DCFDA, which showed only 3-4 fold change, suggesting that QCy-BA dye has a much better dynamic range than DCFDA (FIG. 5(e)).

Further, similar experiments are performed in primary MRC5 cells, which are human lung primary fibroblasts. To induce DNA damage, MRC5 cells are similarly treated with various doses of BrdU and doxorubicin (0.1 μM) for 72 h. After 72 h, probe QCy-BA showed increase in fluorescence compared to control cells in a dose-dependent manner, indicating that the probe can be used to monitor the in situ generated $H_2O_2$ on primary cells as well (FIG. 5(f)). Therefore, above results reveal that QCy-BA is a versatile probe to monitor the elevated levels of $H_2O_2$ in both primary and cancer cells in senescence state.

In addition to QCy-BA, other Formula I compounds also show similar physical & chemical characteristics, and biological activity results when studies related to photophysical properties, switch-on NIR-fluorescence in the presence of DNA, base pair-specific recognition and switch-on fluorescence in the presence of DNA, AT-rich DNA Recognition, Sequence-Specific Recognition of DNA, Fluorescence Imaging, Cytotoxicity Studies, Exogenous and endogenous detection of $H_2O_2$ in HeLa cells, Epidermal growth factor (EGF) produced $H_2O_2$ detection in HeLa cells, Immunofluorescence studies with Formula I compounds for detection of $H_2O_2$ in HeLa cells, Detection limit of $H_2O_2$ in presence of Formula I compounds, detection of ROS using fluorescence plate reader, live cell imaging of MRC5 cells, Fluorescence imaging and cytotoxicity studies of Formula I compounds in presence of $H_2O_2$, monitoring of in situ generated $H_2O_2$ levels by EGF/Nox pathways and post-genotoxic stress in live cells are performed.

In conclusion, a stimuli-responsive, colorimetric and switch-on NIR fluorescence combination probe (compounds of formula I, e.g. QCy-BA in combination with exogenous AT-rich DNA or endogenous nuclear DNA) for $H_2O_2$ is provided by the present disclosure. It is also evident that in QCy-BA, the phenyl boronic acid functionality effectively suppressed the NIR fluorescence of QCy-DT, a DNA minor groove binder and restored selectively in the presence of $H_2O_2$.

NMR and UV-vis absorption study showed selective conversion of QCy-BA to QCy-DT and quinine methide in response to $H_2O_2$ while the solution color changed from yellow to brown for naked eye detection of $H_2O_2$ over other ROS. The fluorescence study demonstrated selective conversion of QCy-BA to QCy-DT in response to $H_2O_2$ stimulus that showed NIR-fluorescence in the presence of AT-rich DNA duplex (Drew-AT). Further, glucose oxidase assay confirmed the use of combination probe QCy-BA ⊂ Drew-AT for probing in situ generated $H_2O_2$ by the oxidation of glucose to gluconic acid. Cell viability and confocal fluorescence imaging of HeLa cells showed the cell permeability, non-toxicity and preferential nuclear staining selectively of the probe in the presence of $H_2O_2$. Furthermore, QCy-BA is sensitive probe to detect normal and in situ generated levels of $H_2O_2$ by EGF/Nox pathways in live cells. Probe QCy-BA is also found to be effective in detection of $H_2O_2$ in the primary cells as well as senescent cancer cells.

The approach of conjugating DNA fluorescence probes with stimuli-responsive appendages opens up a new approach in the development of DNA targeting theranostic prodrugs for targeting disease-related cells. This approach is further expanded to create new stimuli-responsive probes for various biochemical processes including enzymatic activities.

Some of the non-limiting applications of the present compound of Formula I are as follows:

- Diagnostic and therapeutic tool for Reactive Oxidative Species, particularly Hydrogen peroxide.
- Used as a Disease marker and for live cell imaging.
- The probe can be used as (NIR) fluorescence binding markers for biomolecules like DNA and protein.
- The probe is useful for sequence specific recognition of dsDNA in treating gene-related human diseases especially cancer, parasitic and viral infections.
- The intrinsic fluorescence property of the probe makes it a versatile fluorescence marker for molecular biology and immunohistochemistry, fluorescence spectroscopy and microscopy, flow cytometry and DNA quantification applications.
- By choosing suitable donors, formation of an efficient FRET-pair can be arrived at which is useful for monitoring the conformational changes in nucleic acids and proteins.
- Detection and inhibition of parasites.
- This approach of conjugating DNA fluorescence probes with stimuli responsive appendages open up a new approach in the development of DNA targeting theranostic prodrugs for spatiotemporal targeting of disease related cells. This approach can be further expanded to create new stimuli responsive probes for various biochemical processes including enzymatic activities.
- Monitor enzyme activity (Glucose oxidase, Cholinesterase and Sarcosine oxidase etc), multiple applications, chemical biology and research related ROS in primary and cancer cells.

We claim:

1. A compound of Formula I

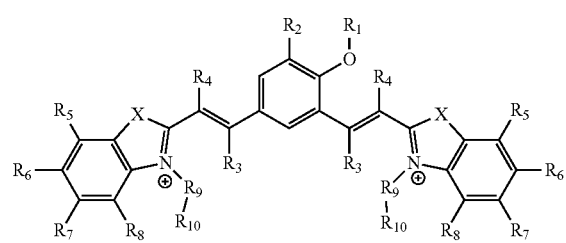

Formula I wherein,

'X' is selected from the group consisting of oxygen, sulphur, and selenium;

'$R_1$' is selected from the group consisting of alkyl chain, allyl group, aryl group, benzyl group, aryl and alky group, acid, amine, ester, methyl phenyl boronic acid, boronic ester, carbonate, phosphate, silane, quaternary ammonium, amide, and imine;

'$R_2$' is selected from the group consisting of H, OH, halogen, alkyl and substituted alkyl, and wherein, the halogen is selected from the group consisting of bromide, chloride, and iodide;

'$R_3$' or '$R_4$' are selected from the group consisting of H, alkyl, aryl, nitrile, acid and halogen, and wherein the halogen is selected from a group comprising, chloride, fluoride, bromide, and iodide;

'$R_5$', '$R_6$', '$R_7$' or '$R_8$' are selected from the group consisting of H, OH, alkyl, aryl, halogen, nitro, sulfonates ($SO_3^-$), and nitrile group;

'$R_9$' is selected from the group consisting of H and —$(CH_2)_n$—, wherein 'n' is 1-6;

'$R_{10}$' is selected from the group consisting of hydrogen, —OH, methyl, amine, terminal alkyne, alkene, alkyl acid, amine acid, and sulfonates ($SO_3^-$).

2. The compound of claim 1, wherein the compound is a stimuli responsive probe and detects reactive oxygen species (ROS).

3. The compound of claim 1 selected from the group consisting of:

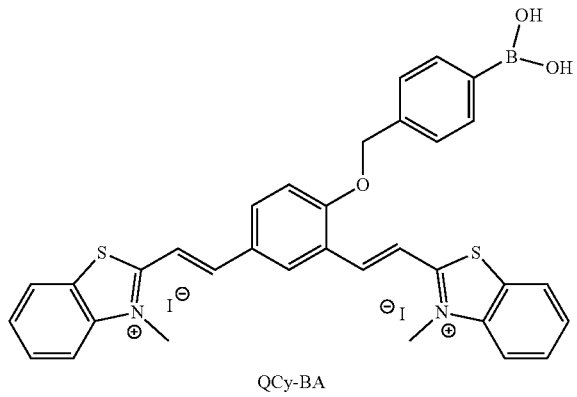

QCy-BA

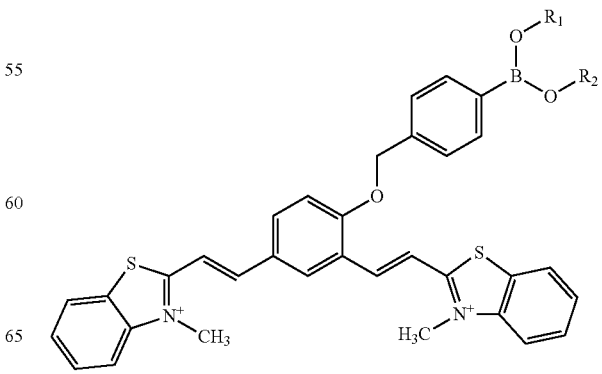

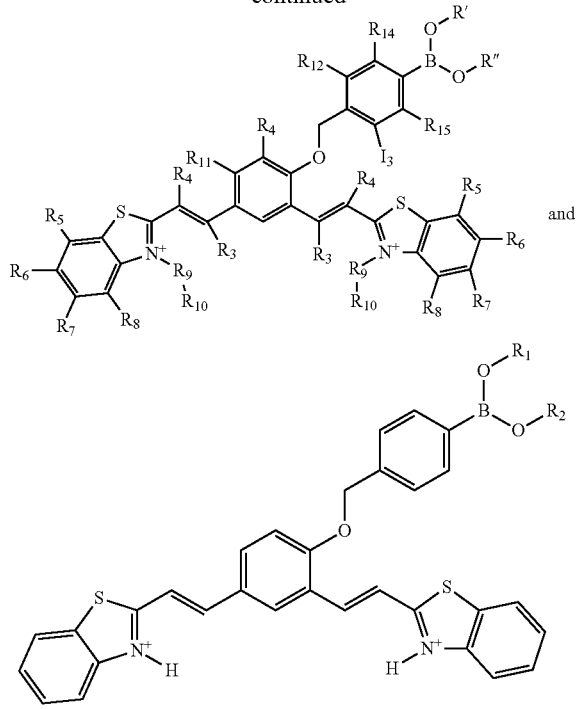

wherein:

R₁ to R₁₄ or R' and R" are independently selected from the group consisting of alkyl, aryl, alicyclic, heterocyclic, O, N, P, S, halogens, cyclic, and acyclic ring system.

4. A pharmaceutical composition comprising the compound of claim 1 along with at least one pharmaceutically acceptable excipient.

5. The pharmaceutical composition of claim 4, wherein the pharmaceutically acceptable excipient is selected from the group consisting of adjuvant, diluent, carrier, granulating agents, binding agents, lubricating agents, disintegrating agent, sweetening agents, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient, and any combination of excipients thereof; and the composition is administered to a subject through modes selected from the group consisting of intravenous administration, intramuscular administration, intraperitoneal administration, hepatoportal administration, intra articular administration and pancreatic duodenal artery administration, and any combination thereof.

6. A method of detecting or quantifying the presence of reactive oxygen species (ROS) in a biological sample, said method comprising the act of contacting the compound of Formula I of claim 1 with the sample and detecting the fluorescence indicative of the presence of ROS in the biological sample.

7. The method of claim 6, wherein said ROS compound is selected from the group consisting of hydrogen peroxide, tertbutyl hydroperoxide, superoxide, hydroxyl radical, tert-butoxy radical, hypochlorite, and ONOO⁻, and wherein the biological sample is cells, tissue, biological fluids, or combinations thereof.

8. A method for detecting or quantifying a ROS compound in vivo in a subject, said method comprising:
   a. administering to a subject, a compound of Formula 1 of claim 1;
   b. allowing said compound of Formula 1 to react with a ROS; and
   c. detecting or quantifying the fluorescence, indicative of the presence of ROS compound in vivo.

9. The method of claim 8, wherein said detecting or quantifying further comprises detecting the location of ROS compound in said subject.

10. The method of claim 6, wherein the detection or quantifying is by technique selected from fluorescence microscopy, fluorescence spectroscopy, confocal laser scanning microscopy, total internal reflection fluorescence microscopy, Near infra-red florescence and combinations thereof; wherein the compound of Formula I is provided as a combination probe with DNA sequences for detecting and quantifying the ROS, and wherein the DNA sequence is exogenous DNA or endogenous nuclear DNA, or a combination thereof; wherein the compound in the presence of ROS is cleaved to release a fluorescent probe quinone cyaninedithiazole (QCy-DT), which is capable of binding to the AT-rich DNA for flourometric detection and quantification of the ROS.

11. A method of diagnosing a disease condition in a subject, said method comprising contacting the compound of Formula I of claim 1 with a sample obtained from the subject.

12. The method of claim 11, wherein the subject is a mammal or a plant, and wherein the sample from mammal is selected from group comprising blood, serum, in-vitro sample, synthetic sample, any bodily fluid and combinations thereof; wherein the disease is selected from a group comprising cancer, cardiovascular dysfunction, neurodegenerative disease, gastroduodenal pathogenesis, inflammatory disorder, metabolic dysfunction of organ, premature aging, any disorder related to ROS, and combinations thereof; wherein the disease is diagnosed by detecting and optionally quantifying reactive oxygen species (ROS) in the sample.

13. A method of treating a disease characterized by abnormal levels of ROS in a subject, said method comprising step of administering the compound of Formula I of claim 1 in said subject to treat the disease.

14. A kit for detecting reactive oxygen species (ROS) in a sample, wherein the kit comprising the compound of claim 1 wherein the compound is present in an amount effective to detect the presence of ROS.

* * * * *